(12) United States Patent
Jeon et al.

(10) Patent No.: US 6,495,583 B1
(45) Date of Patent: Dec. 17, 2002

(54) BENZIMIDAZOLE DERIVATIVES

(75) Inventors: Yoon T. Jeon, Ridgewood, NJ (US); Charles Gluchowski, Wayne, NJ (US)

(73) Assignee: Synaptic Pharmaceutical Corporation, Paramus, NJ (US)

(*) Notice: Subject to any disclaimer, the term of this patent is extended or adjusted under 35 U.S.C. 154(b) by 0 days.

(21) Appl. No.: 10/139,824

(22) Filed: May 6, 2002

Related U.S. Application Data

(63) Continuation of application No. 09/992,947, filed on Nov. 5, 2001, now Pat. No. 6,403,626, which is a division of application No. 09/232,490, filed on Jan. 15, 1999, now Pat. No. 6,316,637, which is a continuation of application No. 08/765,656, filed as application No. PCT/US95/09895 on Aug. 4, 1995, now abandoned, which is a continuation-in-part of application No. 08/285,956, filed on Aug. 4, 1994, now abandoned.

(51) Int. Cl.$^7$ ..................... A61K 31/415; C07D 403/02
(52) U.S. Cl. ..................... 514/394; 548/306.1
(58) Field of Search ................. 514/394; 548/306.1

(56) References Cited

U.S. PATENT DOCUMENTS

| | | |
|---|---|---|
| 3,890,319 A | 6/1975 | Danielewicz et al. |
| 4,000,295 A | 12/1976 | Miesel |
| 4,029,792 A | 6/1977 | Danielewicz et al. |
| 4,192,947 A | 3/1980 | Bauer et al. |
| 4,361,575 A | 11/1982 | Stahle et al. |
| 4,515,800 A | 5/1985 | Cavero et al. |
| 4,588,736 A | 5/1986 | Esser et al. |
| 4,683,229 A | 7/1987 | Demarinis et al. |
| 5,077,292 A | 12/1991 | Gluchowski |
| 5,091,528 A | 2/1992 | Gluchowski |
| 5,478,858 A | 12/1995 | Cupps et al. |
| 5,541,210 A | 7/1996 | Cupps et al. |
| 5,578,607 A | 11/1996 | Cupps et al. |
| 5,691,370 A | 11/1997 | Cupps et al. |
| 6,218,388 B1 | 4/2001 | Boschelli et al. |
| 6,235,765 B1 | 5/2001 | Assman et al. |
| 6,248,770 B1 | 6/2001 | Ries et al. |
| 6,281,237 B1 | 8/2001 | Horvath et al. |
| 6,316,474 B1 | 11/2001 | McCauley et al. |
| 6,329,412 B1 | 12/2001 | Goldstein et al. |

FOREIGN PATENT DOCUMENTS

| | | |
|---|---|---|
| CA | 1112648 | 11/1981 |
| CA | 2078058 | 3/1993 |
| DE | 4325491 | 2/1995 |
| EP | 070084 | 1/1983 |
| EP | 399791 | 11/1990 |
| EP | 419210 | 3/1991 |
| GB | 1410017 | 10/1975 |
| WO | 9203422 | 3/1992 |
| WO | 9203423 | 3/1992 |
| WO | 9218503 | 10/1992 |
| WO | 9221349 | 12/1992 |
| WO | 9325199 | 12/1993 |
| WO | 9516685 | 6/1995 |
| WO | 9823595 | 6/1998 |
| WO | 9846595 | 10/1998 |

OTHER PUBLICATIONS

Chapelo, Christopher B., et al., "Heteroaromatic Analogs of the $\alpha_2$–Adrenoreceptor Partial Agonist Clinidine", *Chemical Abstracts* (1989) 111(3):23456c.

Claxton, et al., "BRL 8242 (2–[–2–Benzimidazolyl]–Amino–2–Imidazoline Dihydrochloride), A New Inhibitor of Dopamine–$\beta$–Hydroxylase With Antihypertensive Activity", *Eur. J. Of Pharm.* (1976) 37: 179–185.

Rouot, Bruno, et al., "Synthesis and Reactivity of p–aminoclonidine", *Chemical Abstracts* (1980) 92(17):146358u.

Van Meel, J.C.A. "Selectivity of some alpha adrenoceptor agonists for peripheral alpha–1 and adrenoceptors in the normotensive rat", *J. of Pharm & Exp. Ther.* (1981) 219(3): 760–767.

*Primary Examiner*—Deborah C. Lambkin
(74) *Attorney, Agent, or Firm*—John P. White; Cooper & Dunham LLP

(57) ABSTRACT

This invention provides compounds having the structure:

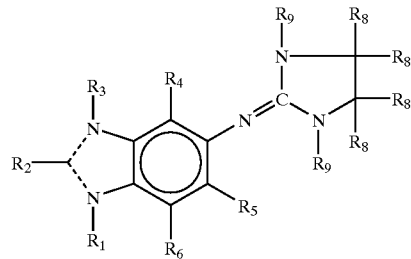

wherein each of $R_1$, $R_2$, $R_3$ and $R_9$ is independently H; straight chain or branched, substituted or unsubstituted $C_1$–$C_7$ alkyl, $C_2$–$C_7$ alkenyl or alkynyl; $C_3$–$C_7$ cycloalkyl or cycloalkenyl; acyl, phenyl, substituted phenyl, or heteroaryl; wherein each dashed line represents a single bond or a double bond with the proviso that if $R_1$ is present, $R_3$ is absent and there is a double bond between N at position 3 and C at position 2 and a single bond between C at position 2 and N at position 1 and if $R_3$ is present, $R_1$ is absent and there is a double bond between N at position 1 and C at position 2 and a single bond between C at position 2 and N at position 3; wherein each of $R_4$, $R_5$ and $R_6$ is independently H, F, Cl, Br, I; straight chain or branched, substituted or unsubstituted $C_1$–$C_7$ alkyl, $C_2$–$C_7$ alkenyl or alkynyl; $C_3$–$C_7$ cycloalkyl or cycloalkenyl; phenyl, substituted phenyl, heteroaryl, —OH, —OR,, —CN, —COR,, —CO$_2$R$_7$, —CON(R$_7$)$_2$, —OCOR$_7$, —SR$_7$, —N(R$_7$)$_2$, —NR$_7$COR$_7$, —(CH$_2$)$_n$OR$_7$, —(CH$_2$)$_n$N(R$_7$)$_2$, —(CH$_2$)$_n$NR$_7$COR$_7$, wherein n is an integer from 1 to 4; and wherein each of R$_7$ and R$_8$ is independently H; straight chain or branched, substituted or unsubstituted $C_1$–$C_7$ alkyl, $C_2$–$C_7$ alkenyl or alkynyl; phenyl or substituted phenyl.

These compounds are selective for cloned human alpha 2 receptors and are useful as analgesic, sedative or anaesthetic agents.

13 Claims, No Drawings

BENZIMIDAZOLE DERIVATIVES

This application is a continuation of U.S. Ser. No. 09/992,947, filed Nov. 5, 2001, now U.S. Pat No. 6,403,626 B1, issued Jun. 11, 2002, which is a divisional of U.S. Ser. No. 09/232,490, filed Jan. 15, 1999, now U.S. Pat. No. 6,316,637 B1, issued Nov. 13, 2001, which is a continuation of U.S. Ser. No. 08/765,656, filed Mar. 25, 1997, now abandoned, which was a §371 national stage application of PCT International Application No. PCT/US95/09895, filed Aug. 4, 1995 on behalf of Synaptic Pharmaceutical Corporation, claiming priority of and a continuation-in-part of U.S. Ser. No. 08/285,956, filed Aug. 4, 1994, now abandoned, the contents of all of which are hereby incorporated by reference into this application. Throughout this application, various references are referred to within parenthesis. Disclosure of these publications in their entireties are hereby incorporated by reference into this application to more fully describe the state of the art to which this invention pertains.

BACKGROUND OF THE INVENTION

Alpha adrenergic receptors are plasma membrane receptors which are located in the peripheral and central nervous systems throughout the body. They are members of a diverse family of structurally related receptors which contain seven putative helical domains and transduce signals by coupling to guanine nucleotide binding proteins (G-proteins). These receptors are important for controlling many physiological functions and, thus, have been important targets for drug development during the past 40 years. Examples of alpha adrenergic drugs include clonidine, phenoxybenzamine and prazosin (for treatment of hypertension), naphazoline (for nasal decongestion), medetomidine (for veterinary analgesia), UK-14,304 and p-aminoclonidine (for glaucoma) . However, most of these drugs produce undesirable side effects which may be due to the their interactions with other receptor subtypes. For example, clonidine is a well known centrally acting antihypertensive agent. However, it also produces untoward side effects such as analgesia, sedation, bradycardia and dry mouth which may be due to its lack of selectivity for a specific receptor subtype, i.e. $\alpha_2$ receptor.

Alpha adrenoceptors were originally proposed to have only two(alpha and beta) subtypes (Berthelsen, S.; Pethinger W. Life Sci. 1977, 21, 595). However, modern molecular biological and pharmacological techniques have led to the identification of at least 6 subtypes ($\alpha_{1a}$, $\alpha_{1b}$, $\alpha_{1c}$, $\alpha_{2a}$, $\alpha_{2b}$ and $\alpha_{2c}$) of the adrenoceptors (Sylund, D. B., Trends Pharmacol. Sci. 1988, 9, 356; Weinshank et al, U.S. Pat. No. 5,053,337, issued Oct. 1, 1991; Bard et al, International Publication No. WO 94/08040, published Apr. 14, 1994).

Among many other therapeutic indications, $\alpha_2$ receptors are believed to modulate pain and behavioral depression by regulating locus coeruleus firing. In addition, $\alpha_2$ receptors are well known to be involved in effects on blood pressure, heart rate, vasoconstriction and glaucoma. However, it is not known which therapeutic. indications are controlled by each of these subtypes.

The effects of alpha-2 receptor agonists on analgesia, anesthesia and sedation have been well documented for past 10 years (Pertovaara, A., Progress in Neurobiology, 1993, 40, 691). For example, systematic administration of clonidine has been shown to produce antinociception in various species including human patients in addition to its well known sedative effects. Intrathecal and epidural administration of clonidine has also proved effective in producing antinociception. Another alpha-2 agonist, Medetomidine, which has better alpha-2/alpha-1 selectivity and is more potent at alpha-2 receptors than clonidine, has been extensively studied for its antinociception effect. In the spinally-initiated heat-induced tail flick test in rats, systematic administration of medetomidine produced a dose-dependent antinociception which could be totally reversed by alpha-2 receptor antagonists, atipamazole or idazoxan. Experimental studies of medetomidine on pain sensitivity in humans also indicated that this agent is very effective on ischemic pains, even though effective drug doses were high enough to produce a sedation and considerable decrease in blood pressure.

Effects of alpha-2 receptor agonists in anaesthetic practice have also been investigated. The sedative effect of alpha-2 agonists is regarded as good component of premedication. Another beneficial effect of alpha-2 agonists in anaesthetic practice is their ability to potentiate the anaesthetic action of other agents and to reduce anaesthetic requirements of other drugs during surgery. Studies shows that premedication with 5 $\mu$g kg$^{-1}$ of oral clonidine administration reduced fentanyl requirements for induction and intubation by 45% in patient undergoing aortocoronary bypass surgery (Ghingnone, M, et al, Anesthesiology 1986, 64, 36).

This invention is directed to novel benzimidazole derivatives which are selective for cloned human alpha 2 receptors. This invention is also related to uses of these compounds as analgesic, sedative and anaesthetic agents. In addition, this invention includes using such compounds for lowering intraocular pressure, and treatment of migraine, hypertension, alcohol withdrawal, drug addiction, rheumatoid arthritis, ischemia, spasticity, diarrhea, nasal decongestion. Furthermore the compounds may be useful as cognition enhancers.

SUMMARY OF THE INVENTION

This invention provides compounds having the structure:

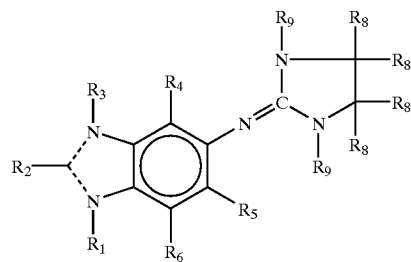

wherein each of $R_1$, $R_2$, $R_3$ and $R_9$ is independently H; straight chain or branched, substituted or unsubstituted $C_1$–$C_7$ alkyl, $C_2$–$C_7$ alkenyl or alkynyl; $C_3$–$C_7$ cycloalkyl or cycloalkenyl; acyl, phenyl, substituted phenyl, or heteroaryl; wherein each dashed line represents a single bond or a double bond with the proviso that if $R_1$ is present, $R_3$ is absent and there is a double bond between N at position 3 and C at position 2 and a single bond between C at position 2 and N at position 1 and if $R_3$ is present, $R_1$ is absent and there is a double bond between N at position 1 and C at position 2 and a single bond between C at position 2 and N at position 3; wherein each of $R_4$, $R_5$ and $R_6$ is independently H, F, Cl, Br, I; straight chain or branched, substituted or unsubstituted $C_1$–$C_7$ alkyl, $C_2$–$C_7$ alkenyl or alkynyl; $C_3$–$C_7$ cycloalkyl or cycloalkenyl; phenyl, substituted phenyl, heteroaryl, —OH, —OR$_7$, —CN, —COR$_7$, —CO$_2$R$_7$, —CON(R$_7$)$_2$, —OCOR$_7$, —SR$_7$, —N(R$_7$)$_2$, —NR$_7$COR$_7$, —(CH$_2$)$_n$OR$_7$, —(CH$_2$)$_n$N(R$_7$)$_2$, —(CH$_2$)$_n$NR$_7$COR$_7$, wherein n is an integer from 1 to 4; and wherein each of R$_7$ and R$_8$ is independently H; straight chain or branched, substituted or unsubstituted C$_1$–C$_7$ alkyl, C$_2$–C$_7$ alkenyl or alkynyl; phenyl or substituted phenyl.

These compounds are selective for cloned human alpha 2 receptors and are useful as analgesic, sedative or anaesthetic agents.

DETAILED DESCRIPTION OF THE INVENTION

The present invention is directed to compounds having the structure:

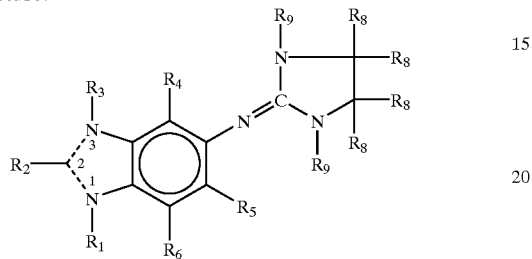

where each of R$_1$, R$_2$, R$_3$ and R$_9$ is independently H; straight chain or branched, substituted or unsubstituted C$_1$–C$_7$ alkyl, C$_2$–C$_7$ alkenyl or alkynyl; C$_3$–C$_7$ cycloalkyl or cycloalkenyl; acyl, phenyl, substituted phenyl, or heteroaryl; where each dashed line represents a single bond or a double bond with the proviso that if R$_1$ is present, R$_3$ is absent and there is a double bond between N at position 3 and C at position 2 and a single bond between C at position 2 and N at position 1 and if R$_3$ is present, R$_1$ is absent and there is a double bond between N at position 1 and C at position 2 and a single bond between C at position 2 and N at position 3; where each of R$_4$, R$_5$ and R$_6$ is independently H, F, Cl, Br, I; straight chain or branched, substituted or unsubstituted C$_7$–C$_7$ alkyl, C$_2$–C$_7$ alkenyl or alkynyl; C$_3$–C$_7$ cycloalkyl or cycloalkenyl; phenyl, substituted phenyl, heteroaryl, —OH, —OR$_7$, —CN, —COR$_7$, —CO$_2$R$_7$, —CON(R$_7$)$_2$, —OCOR$_7$, —SR$_7$, —N(R$_7$)$_2$, —NR$_7$COR$_7$, —(CH$_2$)$_n$OR$_7$, —(CH$_2$)$_n$N(R$_7$)$_2$, —(CH$_2$)$_n$NR$_7$COR$_7$, where n is an integer from 1 to 4; and where each of R$_7$ and R$_8$ is independently H; straight chain or branched, substituted or unsubstituted C$_1$–C$_7$ alkyl, C$_2$–C$_7$ alkenyl or alkynyl; phenyl or substituted phenyl.

The compound may have the following preferred structure:

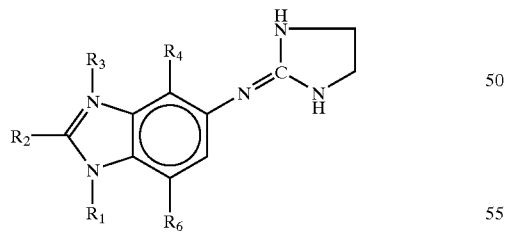

where each of R$_2$, R$_2$, R$_3$, R$_4$ and R$_6$ is defined above.

In addition, the invention further describes compounds having the following structures:

(#1)
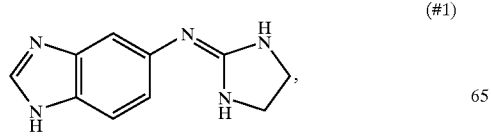

(#2)
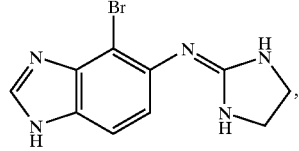

(#3)
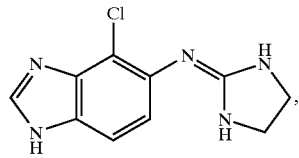

(#4)
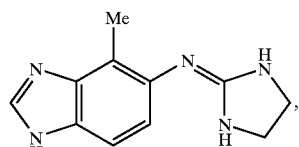

(#18)
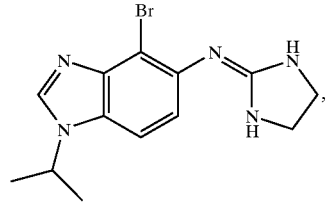

(#44)
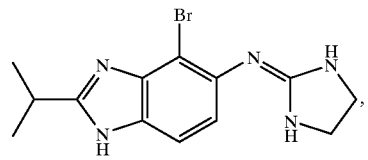

(#53)
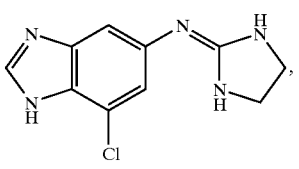

(#52)
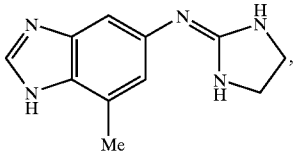

(#60)
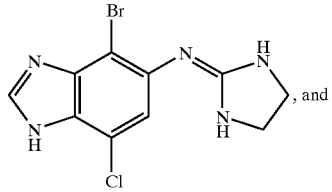, and (#58)
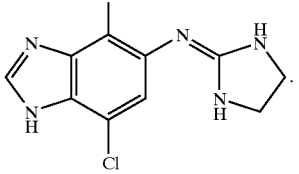

Acid salts of the compounds described above may be also be prepared. The acid salts may be but are not limited to the following HCl, HBr, HI, $H_2SO_4$, $CH_3COOH$, $CF_3COOH$, $HNO_3$, $CF_3SO_3H$, $CH_3SO_3H$, $C_4H_4O_4$, $HO_2CCH=CHCO_2H$, $HO_2CCH=CHCO_2H$, $HO_2CCH(OH)CH(OH)CO_2H$.

The invention also describes a pharmaceutical composition comprising a therapeutically effective amount of the compounds described above and a pharmaceutically acceptable carrier.

The invention further describes a method for treating an alpha-2 adrenergic receptor associated disorder or alleviating pain in a subject which comprises administering to the subject an amount of a compound having the structure:

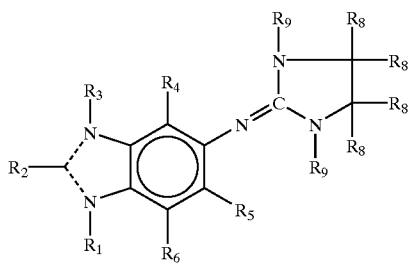

where each of $R_1$, $R_2$, $R_3$, $R_4$, $R_5$, $R_6$, $R_7$, $R_8$ and $R_9$ is defined above.

The invention describes a method for treating an alpha-2 adrenergic receptor associated disorder or alleviating pain in a subject which comprises administering to the subject an amount of a compound having the structure:

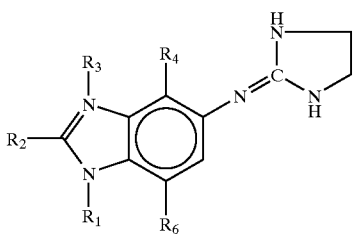

where each of $R_1$, $R_2$, $R_3$, $R_4$ and $R_6$ is defined above.

The invention describes a method for alleviating pain in a subject which comprises administering to the subject an amount of a compound having the structure:

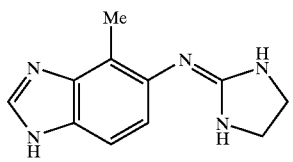

The method described above may be used to treat alpha-2 adrenergic receptor associated disorders such as hypertension, rheumatoid arthritis, ischemia, spasticity, glaucoma, migraines, alcohol withdrawal, drug addiction, diarrhea, or nasal congestion.

The compounds may be administered to a subject suffering from an alpha-2 adrenergic receptor associated disorder. The effective quantity of the compounds described above is from about 0.01 mg/dose to about 100 mg/dose and preferably from about 0.1 mg/dose to about 20 mg/dose. Such dose levels will depend upon the half-life of the compounds see for example Goodman and Gilman's "The Pharmacological Basis of Therapeutics," Eighth Edition, 1990, Pergamon Press, pages 3–32.

Administration for the above compounds may be by any conventional route of administration, including, but not limited to, intravenous, intramuscular, oral, ophthalmic, subcutaneous, intratumoral, intradermal, and parenteral.

The present invention also provides compounds useful for preparing a pharmaceutical composition comprising any of the compounds disclosed herein and a pharmaceutically acceptable carrier. The composition may contain between 0.1 mg and 500 mg of any of the compounds, and may be constituted in any form suitable for the mode of administration selected.

The compounds may be administered neat or with a pharmaceutical carrier to a patient in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired.

The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intraperitoneal or subcutaneous injection. Sterile solutions can also be administered intravenously.

The compounds may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The compound can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The compound can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Optimal dosages to be administered may be determined by those skilled in the art, and will vary with the particular compound in use, the strength of the preparation, the mode of administration, and the advancement of the disease condition. Additional factors depending on the particular subject being treated will result in a need to adjust dosages, including subject age, weight, gender, diet, and time of administration.

This invention will be better understood from the Experimental Details which follow. However, one skilled in the art will readily appreciate that the specific methods and results discussed are merely illustrative of the invention as described more fully in the claims which follow thereafter.

Experimental Details

General Methods

Four general synthetic methods were used to synthesize the compounds described herein. These methods are illustrated in Reaction Schemes 1–4.

The compounds herein have been prepared using synthetic sequences shown in Schemes 1–4. C-4 halogen substituted 5-aminobenzimidazoles were obtained from commercially available 5-nitrobenzimidazole by the sequence of hydrogenation and halogenation. C-4 alkyl substituted analogs were prepared in a similar reaction sequence in which alkyl group was incorporated using a Grignard reaction (Scheme 1). Reaction of 5-aminobenzimidazole with 2-imidazoline-2-sulfonic acid (ISA) which was obtained from 2-imidazolinethione (Gluchowski, C. U.S. Pat. No. 5,130,441) provides access to 2-aminoimidazolines in high yield (45–95%). C-2 substituted 5-nitrobenzimidazoles were prepared by condensation of 4-nitro-1,2-phenylenediamine with corresponding acids (Scheme 2). C-2 substituted 5-nitrobenzimidazoles were subjected to the same reaction sequence as Scheme 1 to provide the desired final product. Reaction of alkyl halides with 5-nitrobenzimidazole in the presence of NaH provided both N-1 and N-3 substituted benzimidazoles (Scheme 3). The reaction mixtures were subjected to hydrogenation ($H_2$/Pd-C) to produce the corresponding amines, which were separated on column chromatography. Each amine was subjected to the reaction sequence described in Scheme 1 to provide the final product.

Preparation of C-7 substituted benzimidazoles is illustrated in Scheme 4. Halogenation of 2,4-dinitroaniline provided 6-halogen substituted anilines, which were subjected to hydrogenation and condensation in formic acid to provide 7-halosubstituted 5-aminobenzimidazoles. These intermediates were coupled to ISA to provide the desired products. C-7 alkyl substituted benzimidazoles were prepared using a similar sequence of reactions. Accordingly, 6-bromo-2,4-dinitroaniline was converted to 6-alkyl or aryl substituted analogs by the Pd(II) catalyzed coupling reaction. Conversion of alkyl substituted anilines to benzimidazoles was carried out in same reaction sequences described in Scheme 2.

Scheme 1
Synthesis of C-4 substituted benzimidazoles.

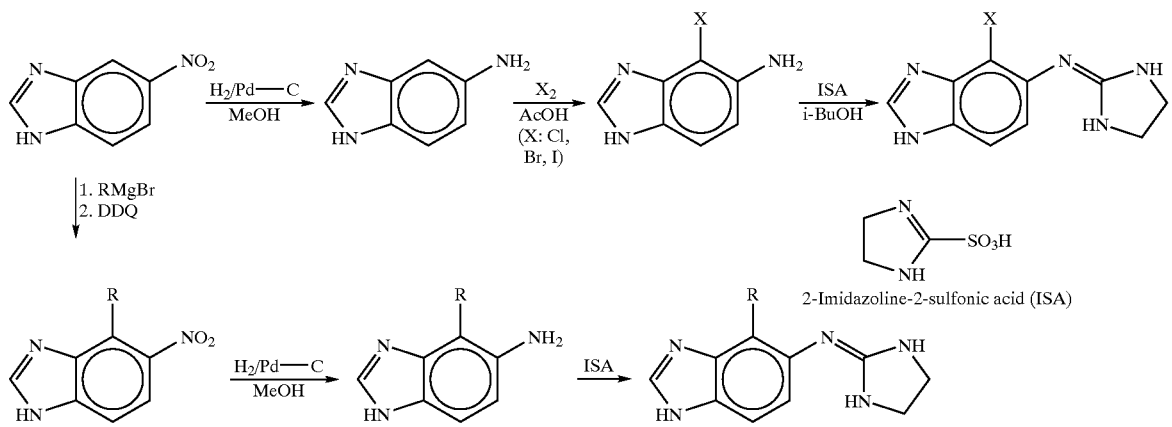

Scheme 2
Synthesis of C-2 substituted benzimidazoles.

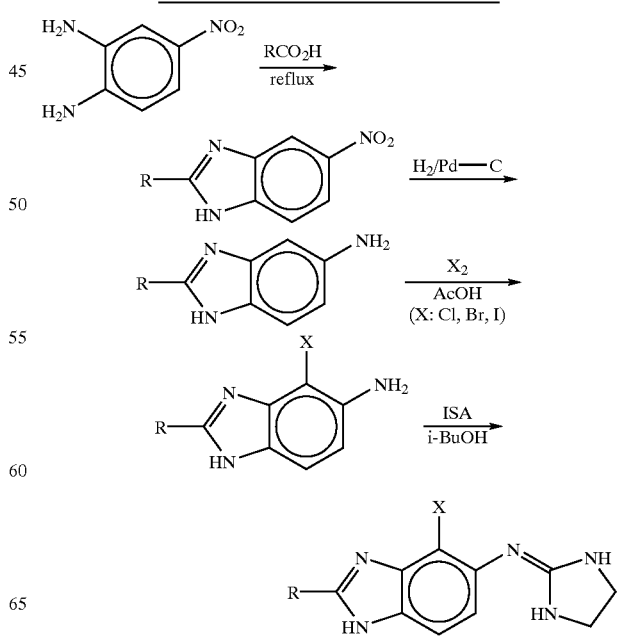

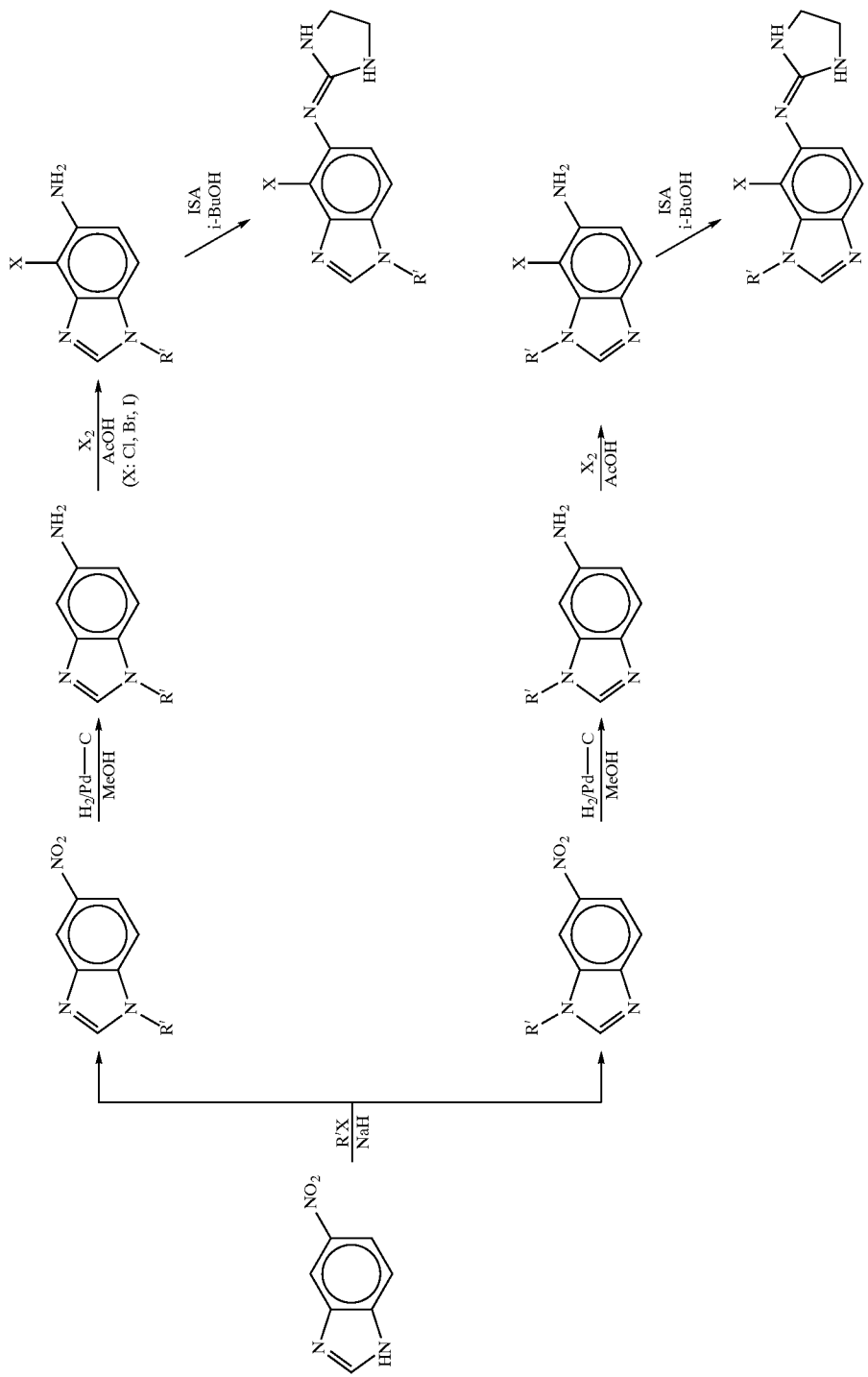

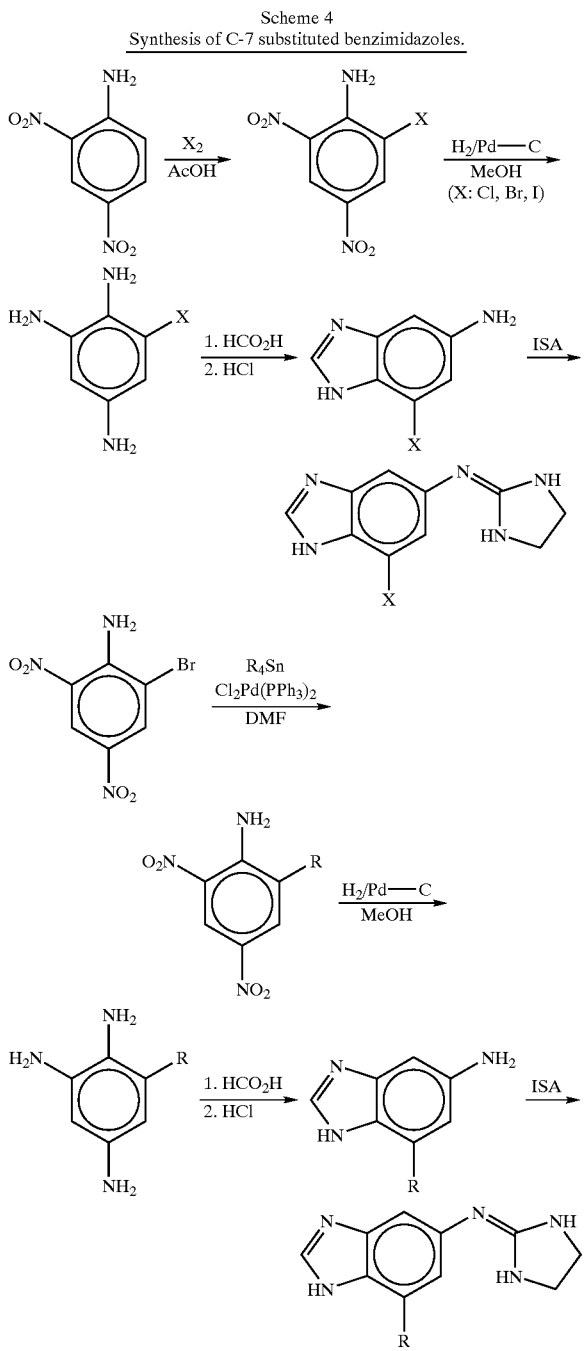

Scheme 4
Synthesis of C-7 substituted benzimidazoles.

EXAMPLE 1

5-(2-Imidazolin-2-ylamino)benzimidazole (#1)

5-Aminobenzimidazole. A solution of 5-nitrobenzimidazole (4.0 g, 25 mmol) and 10% Pd/C (0.5 g) was stirred under $H_2$ for 12 h. The reaction mixture was filtered through Celite-assisted funnel and concentrated in vacuo, yielding 3.2 g (25 mmol, >95%) of the desired product, which was characterized by NMR and subjected to following reactions without further purification.

2-Imidazoline-2-sulfonic acid (ISA). ISA was prepared according to the procedure described in literature (Gluchowski, C. U.S. Pat. No. 5,130,441, 1992). To a solution of 2-imidazolinethione (6.6 g, 65 mmol), sodium molybdate(IV) dihydrate (0.5 g, 2.1 mmol) and NaCl (1.5 g) in 150 ml of distilled water was added 30% of $H_2O_2$ (50 ml, 450 mmol) for 1 h at −10° C. The reaction mixture was stored at −20° C. for 12 h and then reaction temperature was slowly warmed up to 25° C. The white crystal obtained was filtered and dried in vacuo to provide 2.8 g (21 mmol, 32%) of the acid. The compound was used in the examples noted below.

5-(2-Imidazolin-2-ylamino)benzimidazole. A solution of 5-aminobenzimidazole (1.0 g, 7.5 mmol) and ISA (2.5 g, 18.8 mmol) in 10 ml of isobutanol was stirred at reflux for 12 h. The reaction mixture was concentrated in vacuo to yield an oily residue which was subjected to silica gel column chromatography (20% $NH_3$ sat'd MeOH/EtOAc) to produce 0.77 g (3.8 mmol, 53%) of the product. The product obtained was converted to the fumarate salt and recrystallized from MeOH to afford 0.21 g (27%) of the product as a white solid: mp 196–198° C.; Anal. Calc. for $C_{10}H_{11}N_5 \cdot 1.0C_4H_4O_4 \cdot 1.3H_2O$ requires C, 49.62; H, 4.65; N, 20.67. Found: C, 49.65; H, 5.73; N, 20.53.

EXAMPLE 2

4-Bromo-5-(2-imidazolin-2-ylamino)benzimidazole (#2)

4-Bromo-5-aminobenzimidazole. To a solution of 5-aminobenzimidazole (3.3 g, 2.3 mmol) in 30 ml of ACOH was added bromine (0.055 ml, 1.1 mmol) in a portion and resulting reaction mixture was stirred for 0.5 h at 25° C. Reaction mixture was concentrated in vacuo, yielding a dark brown solid which was subjected to silica gel column chromatography ($NH_3$ saturated 10% MeOH/EtOAc) to yield 0.22 g (0.97 mmol, 42%) of the desired product.

4-Bromo-5-(2-imidazolin-2-ylamino)benzimidazole. A solution of 4-bromo-5-aminobenzimidazole (0.22 g, 0.97 mmol) and ISA (0.34 g, 2.5 mmol) in 5 ml of isobutanol was stirred at reflux for 12 h. Reaction mixture was concentrated in vacuo and subjected to silica gel column chromatography ($NH_3$ saturated 20% MeOH/EtOAc) to yield 0.23 g (0.83 mmol, 84%) of the product. The product obtained was converted to the fumarate salt and recrystallized from MeOH to afford 0.12 g (30%) of the product as a white solid: mp 199–202° C.; Anal. Calc. for $CO_{10}H_{10}N_5Br \cdot 1.0C_4H_4 \cdot 0.7H_2O$ requires C, 41.13; H, 3.80; N, 17.13. Found: C, 41.60; H, 3.81; N, 16.97.

EXAMPLE 3

4-Chloro-5-(2-imidazolin-2-ylamino)benzimidazole (#3)

4-Chloro-5-aminobenzimidazole. To a solution of 5-aminobenzimidazole (1.0 g, 7.5 mmol) in 20 ml of AcOH was added $Cl_2$ saturated AcOH solution until it produced a precipitation. The reaction mixture was concentrated in vacuo, yielding a dark residue which was subjected to column chromatography ($NH_3$ sat'd 30% MeOH/EtOAc) to yield 120 mg (0.72 mmol) of 4-chloro-5-aminobenzimidazole.

4-Chloro-5-(2-imidazolin-2-ylamino)benzimidazole. The amine (120 mg, 0.72 mmol) was mixed with ISA (250 mg, 1.8 mmol), and resulting mixture was stirred for 12 h at reflux. Column chromatographic separation ($NH_3$ sat'd 30% MeOH/EtOAc) of the reaction mixture yielded 140 mg (0.62 mmol, 87%) of the desired product. The product obtained was converted to the fumarate salt and recrystallized from EtOH to afford 50 mg (20%) of the product as a white solid: Mp 207–208° C.; Anal. Calc. for $C_{10}H_{10}N_5Cl.1.0C_4H_4O_4.0.6H_2O$ requires C, 46.38; H 4.23; N, 19.32. Found: C, 46.32; H, 4.23; N, 19.47.

EXAMPLE 4

4-Methyl-5-(2-imidazolin-2-ylamino)benzimidazole (#4)

4-Methyl-5-aminobenzimidazole. A solution of 4-bromo-5-aminobenzimidazole (180 mg, 0.84 mmol), tetramethyltin (330 mg, 2.4 mmol) and bis(triphenylphosphine)palladium (II) chloride (20 mg) in 5 ml of anhydrous DMF was placed in sealed tube and stirred for 12 h at 145° C. The reaction mixture was concentrated in vacuo, yielding an oily residue which was subjected to column chromatographic separation ($NH_3$ sat'd 10% MeOH/EtOAc) to yield 140 mg (0.83 mmol, >95%) of 4-methyl-5-aminobenzimidazole.

4-Methyl-5-(2-imidazolin-2-ylamino)benzimidazole. The amine obtained was placed in flask with ISA (0.38 g, 2.5 mmol) and 5 ml of isobutanol, and resulting mixture was stirred at reflux for 12 h. Column chromatographic separation ($NH_3$ sat'd 10% MeOH/EtOAc) of the reaction mixture provided 0.15 g (0.71 mmol, 84%) of the desired product. The product obtained was converted to the fumarate salt and recrystallized from MeOH to afford 92 mg (25%) of the product as a white solid: mp 155–157° C.; Anal. Calc. for $C_{11}H_{13}N_5.1.5C_4H_4O_4.0.5H_2O$ requires C, 52.08; H, 4.96; N, 17.86. Found: C, 52.08; H, 4.97; N, 17.80.

EXAMPLE 5

4-Iodo-5-(2-imidazolin-2-ylamino)benzimidazole (#5)

4-Iodo-5-aminobenzimidazole. To a solution of 5-aminobenzimidazole (0.6 g, 4.5 mmol) and $Hg(OAc)_2$ (1.72 g, 5.5 mmol) in 20 ml of ACOH was added a solution of $I_2$ until solution produces a precipitation. The reaction mixture was concentrated in vacuo, yielding an oily residue which was subjected to column chromatographic separation ($NH_3$ sat'd 10% MeOH/EtOAc) to produce 0.30 (1.2 mmol, 26%) g of 4-iodo-5-aminobenzimidazole.

4-Iodo-5-(2-imidazolin-2-ylamino)benzimidazole. A solution of the amine (0.30 g, 1.1 mmol) and ISA (0.62 g, 4.4 mmol) was stirred at reflux for 12 h. Column chromatographic separation of the reaction mixture ($NH_3$ sat'd 20% MeOH/EtOAc) provided 0.12 g (0.34 mmol, 31%) of the desired product. The product obtained was converted to the fumarate salt and recrystallized from EtOH to afford 0.12 g (20%) of the product as a white solid:.mp 256° C.; Anal. Calc. for $C_{10}H_{10}N_5I.2.0C_4H_4O_4.1.0H_2O$ requires C, 37.45; H, 3.49; N, 12.13. Found: C, 37.52; H, 3.51; N, 12.62.

EXAMPLE 6

4-Ethyl-5-(2-imidazolin-2-ylamino)benzimidazole (#6)

4-Ethyl-5-aminobenzimidazole. To a solution of 5-nitrobenzimidazole (2.8 g, 17 mmol) in THF was added 16 ml of EtMgBr solution (48 mmol) and reaction mixture was stirred for 2 h at −15° C. A solution of tetrachloro-1,4-benzoquinone (8.8 g, 36 mmol) in THF was added dropwise into reaction mixture, which was allowed to warm up to 25° C. over 1 h. Silica gel(20 g) was added into reaction mixture and solvent was removed in vacuo to provide a brown silica gel powder which was subjected to column chromatography (EtOAc, meat) to provide 1.7 g (8.9 mmol, 52%) of 4-ethyl-5-nitrobenzimidazole, which was subsequently subjected to hydrogenation ($H_2$, Pd/c) to yield 1.32 g (8.2 mmol) of 4-ethyl-5-aminobenzimidazole.

4-Ethyl-5-(2-imidazolin-2-ylamino)benzimidazole. A solution of the amine (0.71 g, 4.3 mmol) and ISA (0.75 g, 5.6 mmol) in 10 ml of isobutanol was stirred at reflux for 12 h. The reaction mixture was concentrated in vacuo, yielding an oil, which was subjected to column chromatography ($NH_3$ sat'd 30% EtOH/EtOAc) to yield 0.26 g (1.2 mmol, 28%) of the desired product. The product obtained was converted to the fumarate salt and recrystallized from MeOH to afford 0.22 g (16%) of the product as a light brown solid: mp 238–239° C.; Anal. Calc. is for $C_{12}H_{15}N_5.1.0C_4H_4O_4$ requires C, 55.60; H, 5.55; N, 20.28. Found: C, 54.63; H, 5.70; N, 19.46.

EXAMPLE 7

4-n-Propyl-5-(2-imidazolin-2-ylamino) benzimidazole (#7)

4-n-Propyl-5-aminobenzimidazole. To a solution of 5-nitrobenzimidazole (2.3 g, 14 mmol) was added 14 ml of n-PrMgBr solution (42 mmol) and reaction mixture was stirred for 2 h at −15° C. The reaction was quenched by adding a solution of tetrachloro-1,4-benzoquinone (4 g, 16 mmol) in 10 ml of THF. The reaction mixture was concentrated in vacuo to provide an oil, which was subjected to column chromatographic separation (EtOAc, neat) to provide 1.4 g (7.2 mmol, 52%) of 4-n-propyl-5-nitrobenzimidazole, which was converted to the corresponding amine (1.2 g, >95%) by hydrogenation($H_2$, Pd/C).

4-n-Propyl-5-(2-imidazolin-2-ylamino)benzimidazole. The amine (1.2 g, 14 mmol) was stirred with ISA (1.5 g, 11.2 mmol) at reflux for 12 h. Concentration of reaction mixture produced an oily residue, which was subjected to column chromatographic separation ($NH_3$ sat'd 30% MeOH/EtOAc) to provide 0.63 g (2.6 mmol, 37%) of the desired product. The product obtained was converted to the fumarate salt and recrystallized from EtOH to afford 0.45 g (16%) of the product as a light brown solid: mp 229–230° C.

EXAMPLE 8

4-n-Butyl-5-(2-imidazolin-2-ylamino)benzimidazole (#8)

4-n-Butyl-5-aminobenzimidazole. To a solution of 5-nitrobenzimidazole (0.41 g, 2.5 mmol) was added a solution of n-BuLi (7.5 mmol) and reaction mixture was stirred for 1 h at 0° C. The reaction mixture was quenched by adding a few drops of $H_2O$ and concentrated in vacuo yielding an oil which was subjected to silica gel column chromatography (5% MeOH/ EtOAC) to provide 0.13 g of 4-n-butyl-5-nitrobenzimidazole and 0.19 g of 4-n-butyl-5-aminobenzimidazole. The nitrobenzimidazole was converted to the amine in hydrogenation ($H_2$/Pd-C) to provide 0.28 g (1.5 mmol, 60%) of the desired product.

4-n-Butyl-5-(2-imidazolin-2-ylamino)benzimidazole. The amine (0.28 g, 1.5 mmol) was refluxed with ISA (0.50 g, 3.7 mmol) in isobutanol for 12 h. Column chromatographic separation of reaction mixture ($NH_3$ sat'd 20% MeOH/EtOAc) provided 0.21 g (0.81 mmol, 54%) of the product. The product obtained was converted to the fumarate salt and recrystallized from isopropanol to afford 0.38 g (49%) of the product as a foamy solid: mp 96° C.; Anal. Calc. for $C_{14}H_{19}N_5.2.0C_4H_4O_4$. requires C, 55.68; H. 5.86; N, 16.23. Found: C, 55.98; H, 5.68; N, 16.49.

EXAMPLE 9

1-Methyl-5-(2-imidazolin-2-ylamino)benzimidazole (#9)

1- and 3-Methyl-5-aminobenzimidazole. A solution of 5-nitrobenzimidazole (3.0 g, 18.4 mmol) in 100 ml of THF was stirred with NaH (2.7 g, 36.8 mmol) for 0.5 h at 25° C. To the solution was added methyl iodide (2.0 ml, 20.3 mmol) and resulting mixture was stirred for 12 h. The reaction mixture was concentrated in vacuo to provide an oil, which was dissolved in 200 ml of MeOH and stirred with 0.3 g of 10% Pd/C under $H_2$ for 12 h. The reaction mixture was filtered and concentrated in vacuo, yielding a dark oily residue which was subjected to column chromatography (3% MeOH/CHCl$_3$) to provide 0.69 g (3.9 mmol, 21%) of 1-methyl-5-aminobenzimidazole and 0.36 g (2.0 mmol, 11%) of 3-methyl-5-aminobenzimidazole.

1-Methyl-5-(2-imidazolin-2-ylamino)benzimidazole A solution of 1-methyl-5-aminobenzimidazole (0.15 g, 1.1 mmol) and ISA (.30 g, 2.2 mmol) in 3 ml of isobutanol was stirred at reflux for 12 h. The reaction mixture was concentrated in vacuo, yielding an oily residue which was purified on silica gel column chromatography (NH$_3$ sat'd 20% isopropanol/EtOAc) to yield 0.12 g (0.56 mmol, 51%) of the desired product. The product obtained was converted to the fumarate salt and recrystallized from isopropanol to afford 0.11 g (30%) of the product as a white crystal: mp 210–211° C.; Anal. Calc. for $C_{11}H_{13}N_5 \cdot 1.0C_4H_4O_4 \cdot 0.3H_2O$ requires C, 35.36; H, 5.28; N,20.74. Found: C, 53.67; H, 5.13; N, 20.70.

EXAMPLE 10

1-Methyl-4-bromo-5-(2-imidazolin-2-ylamino) benzimidazole (#10)

1-Methyl-4-bromo-5-aminobenzimidazole. To a solution of 1-methyl-5-aminobenzimidazole (0.36 g, 2.4 mmol) in 10 ml of AcOH was added Br$_2$ (0.12 ml). The reaction mixture was stirred for 1 h at 25° C. and concentrated in vacuo, yielding an oil which was subjected to column chromatography (NH$_3$ sat'd 3% MeOH/CHCl$_3$) to yield 0.27 g (1.2 mmol, 50%) of the desired product.

1-Methyl-4-bromo-5-(2-imidazolin-2-ylamino) benzimidazole. Isobutanolic solution of the amine (0.27 g, 1.2 mmol) and ISA (0.6 g, 4.5 mmol) was stirred at reflux for 12 h. The reaction mixture was concentrated in vacuo, yielding an oily residue which was subjected to column chromatography (NH$_3$ sat'd 20% MeOH/EtOAc) to yield 0.33 g (1.1 mmol, 92%) of the expected product. The product obtained was recrystallized from EtOH to afford 0.21 g (64%) of the product as a white crystal: mp 237–238° C.; Anal. Calc. for $C_{11}H_{12}N_5Br \cdot 1.75H_2O$ requires C, 40.57; H, 4.80; N. 21.50. Found: C, 40.98; H, 4.81; N, 21.41.

EXAMPLE 11

3-Methyl-5-(2-imidazolin-2-ylamino)benzimidazole. (#11)

A solution of 3-methyl-5-aminobenzimidazole (0.20 g, 1.5 mmol) and ISA (0.45 g, 3.4 mmol) was stirred at reflux for 12 h. The reaction mixture was concentrated in vacuo and purified on column chromatography (NH$_3$ sat'd 20% MeOH/EtOAc) to yield 0.19 g (0.88 mmol, 59%) of the product. The product obtained was converted to the fumarate salt and recrystallized from MeOH to afford 0.31 g (46%) of the product as a white crystal: mp 202–204° C.; Anal. Calc. for $C_{11}H_{13}N_5 \cdot 2.0C_4H_4O_4$ requires C, 51.01; H. 4.73; N,15.65. Found: C, 51.65; H, 4.76; N, 15.78.

EXAMPLE 12

3-Methyl-4-bromo-5-(imidazolin-2-ylamino) benzimidazole (#12)

3-Methyl-4-bromo-5-aminobenzimidazole. To a solution of 3-methyl-5-aminobenzimidazole (0.27 g, 1.8 mmol) in 10 ml of AcOH was added Br$_2$ (0.10 ml). The reaction mixture was stirred for 1 h at 25° C. and concentrated in vacuo, yielding an oil which was subjected to column chromatography (NH$_3$ sat'd 3% MeOH/CHCl$_3$) to yield 0.14 g (0.62 mmol, 35%) of the desired product.

3-Methyl-4-bromo-5-(imidazolin-2-ylamino) benzimidazole. A solution of 3-methyl-4-bromo-5-aminobenzimidazole (0.31 g, 1.4 mmol) and ISA (0.6 g, 4.5 mmol) in 10 ml of isobutanol was stirred at reflux for 12 h. Oily residue obtained was subjected to column chromatography (NH$_3$ sat'd 20% isopropanol/EtOAc) to yield 0.39 g (1.3 mmol, 93%) of the desired product. The product obtained was converted to the fumarate salt and recrystallized from MeOH to afford 0.50 g (68%) of the product as a white solid: mp 209–210° C.; Anal. Calc. for $C_{11}H_{12}N_5Br \cdot 2.0C_4H_4O_4$. requires C, 43.36; H, 3.83; N, 13.31. Found: C, 43.66; H, 3.84; N, 13.10.

EXAMPLE 13

1-Propyl-5-(2-imidazolin-2-ylamino)benzimidazole (#13)

1- and 3-Propyl-5-aminobenzimidazole. A solution of 5-nitrobenzimidazole (3.6 g, 23 mmol) in 100 ml of THF was stirred with NaH (1.5 g, 33 mmol) for 0.5 h at 25° C. To the solution was added allyl bromide (4.8 ml, 57 mmol) and resulting mixture was stirred for 12 h. The reaction mixture was concentrated in vacuo to provide an oil, which was subjected to column chromatography to yield 4.0 g (19.7 mmol, 89%) of a mixture of 1- and 3-allyl-5-nitrobenzimidazole. The nitrobenzimidazole mixture was stirred in 100 ml of MeOH for 12 under H$_2$ in the presence of 10% Pd/C. The reaction mixture was filtered and concentrated in vacuo to provide oily residue which was subjected to column chromatography (50% Hexane/EtOAc) to provide 1.2 g (7.0 mmol) of 1-propyl-5-aminobenzimidazole and 1.1 g (6.4 mmol) of 3-propyl-5-aminobenzimidazole.

1-Propyl-5-(2-imidazolin-2-ylamino)benzimidazole. Reaction of 1-propyl-5-aminobenzimidazole (1.2 g, 7.0 mmol) and ISA (2.2 g, 16 mmol) provided 1.6 g (6.6 mmol, 94%) of the expected product after column chromatographic separation. The product obtained was converted to the fumarate salt and recrystallized from MeOH to afford 2.1 g (76%) of the product as a light brown solid: mp 206–207° C.; Anal. Calc. for $C_{13}H_{17}N_5 \cdot 1.5C_4H_4O_4$ requires C, 54.67; H, 5.55; N, 16.98. Found: C, 54.60; H, 5.49; N, 17.16.

EXAMPLE 14

1-Propyl-4-bromo-5-(imidazolin-2-ylamino) benzimidazole (#14)

1-Propyl-4-bromo-5-aminobenzimidazole. To a solution of 1-propyl-5-aminobenzimidazole (1.2 g, 7.1 mmol) in 10 ml of AcOH was added solution of Br$_2$ in AcOH until it produces a precipitation. The reaction mixture was concentrated in vacuo to provide a brown solid which was subjected to column chromatography (5% NH$_3$ sat'd MeOH/CH$_2$Cl$_2$) to provide 0.83 g (3.4 mmol, 48%) of the product.

1-Propyl-4-bromo-5-(imidazoline-2-ylamino) benzimidazole. A reaction of the amine (0.83 g, 3.4 mmol) and ISA (1.3 g, 9.7 mmol) produced 0.44 g (1.3 mmol, 38%) of the product after chromatographic separation. The product obtained was converted to the fumarate salt and recrystallized from isopropanol to afford 0.32 g (25%) of the product as a light brown solid: mp 206–207° C.; Anal. Calc. for C$_{13}$H$_{16}$N$_5$Br.0.5C$_4$H$_4$O$_4$.0.5H$_2$O requires C, 46.29; H, 4.92; N, 17.99. Found: C, 46.66; H, 4.86; N, 17.60.

EXAMPLE 15

3-Propyl-5-(2-imidazolin-2-ylamino)benzimidazole. (#15)

A reaction of 3-propyl-5-aminobenzimidazole (1.0 g, 5.8 mmol) and ISA (1.9 g, 14 mmol) provided 1.3 g (5.0 mmol, 87%) of product after column chromatography. The product obtained was converted to the fumarate salt and recrystallized from isopropanol to afford 0.32 g (25%) of the product as a white solid: mp 198–199° C.; Anal. Calc. for C$_{13}$H$_{17}$N$_5$.1.0C$_4$H$_4$O$_4$ requires C, 56.82; H, 5.89; N. 19.49. Found: C, 57.12; H, 5.91; N, 19.61.

EXAMPLE 16

3-Propyl-4-bromo-5-(2-imidazolin-2-ylamino) benzimidazole (#16)

3-Propyl-4-bromo-5-aminobenzimidazole. To a solution of 3-propyl-5-aminobenzimidazole (0.71 g, 4.3 mmol) in 10 ml of ACOH was added solution of Br$_2$ in ACOH until it produces a precipitation. The reaction mixture was concentrated in vacuo to provide a brown solid which was subjected to column chromatography (5% NH$_3$ sat'd MeOH/CH$_2$Cl$_2$) to provide 0.40 g (1.6 mmol, 37%) of the product.

3-Propyl-4-bromo-5-(2-imidazolin-2-ylamino) benzimidazole. A reaction of 3-propyl-4-bromo-5-aminobenzimidazole (0.40 g, 1.6 mmol) and ISA (0.7 g, 5.2 mmol) provided 0.32 g (1.3 mmol, 81%) of product after column chromatography. The product obtained was converted to the fumarate salt and-recrystallized from isopropanol to afford 0.30 g (58%) of the product as a white solid: mp 179–181° C.; Anal. Calc. for C$_{13}$H$_{16}$N$_5$Br.1.0C$_4$H$_4$O$_4$ requires C, 46.59; H, 4.60; N, 15.98. Found: C, 46.36; H, 4.49; N, 15.81.

EXAMPLE 17

1-Isopropyl-5-2-imidazolin-2-ylamino) benzimidazole (#17)

1- and 3-Isopropyl-5-aminobenzimidazole. A reaction of 5-nitrobenzimidazole (4.8 g, 29 mmol) and isopropyl bromide (3.7 ml) in a procedure described in Example 9 produces 5.1 g (23 mmol, 81%) of a mixture of 1- and 3-isopropyl-5-nitrobenzimidazole, which was converted to the corresponding amines in hydrogenation (H$_2$/Pd-C). The amine mixture was subjected to column chromatography (10% i-PrOH/CH$_2$Cl$_2$) to provide 1.5 g (7.9 mmol, 27%) of 1-Isopropyl-5-aminobenzimidazole and 2.4 g (12.6 mmol, 44%) of 3-isopropyl-5-aminobenzimidazole.

1-Isopropyl-5-(2-imidazolin-2-ylamino)benzimidazole. Reaction of 1-isopropyl-5-aminobenzimidazole (0.41 g, 2.3 mmol) and ISA (0.70 g, 5.2 mmol) provided 0.37 g (1.5 mmol, 66%) of the expected product after column chromatographic separation. The product obtained was converted to the fumarate salt and recrystallized from isopropanol to afford 0.27 g (24%) of the product as a light brown solid: mp 185–186° C.; Anal. Calc. for C$_{13}$H$_{17}$N$_5$.2.0C$_4$H$_4$O$_4$ requires C, 52.83; H, 5.70; N,14.67. Found: C, 53.32; H, 5.63; N, 14.97.

EXAMPLE 18

1-Isopropyl-4-bromo-5-(2-imidazolin-2 ylamino) benzimidazole (#18)

1-Isopropyl-4-bromo-5-aminobenzimidazole. To a solution of 1-isopropyl-5-aminobenzimidazole (2.4 g, 14 mmol) in 20 ml of AcOH was added solution of Br$_2$ in AcOH until it produces a precipitation. The reaction mixture was concentrated in vacuo to provide a brown solid which was subjected to column chromatography (5% NH$_3$ sat'd MeOH/CH$_2$Cl$_2$) to provide 1.2 g (4.5 mmol, 35%) of the product.

1-Isopropyl-4-bromo-5-(2-imidazolin-2-ylamino) benzimidazole. A reaction of the amine (0.86 g, 3.4 mmol) and ISA (0.90 g, 6.7 mmol) produced 0.67 g (2.1 mmol, 61%) of the product after chromatographic separation. The product obtained was converted to the fumarate salt and recrystallized from isopropanol to afford 0.55 g (37%) of the product as a light brown solid: mp 187–188° C.; Anal. Calc. for C$_{13}$H$_{16}$N$_5$Br.1.0C$_4$H$_4$O$_4$ requires C, 46.59; H, 4.60; N, 15.98. Found: C, 46.35; H, 4.49; N, 15.82.

EXAMPLE 19

1-Isopropyl-4-Iodo-5-(2-imidazolin-2-ylamino) benzimidazole (#19)

1-Isopropyl-4-iodo-5-aminobenzimidazole. To a solution of 1-isopropyl-5-aminobenzimidazole (0.70 g, 3.7 mmol) and Hg(OAc)$_2$ (2.1 g, 5.6 mmol) in 10 ml of AcOH was added solution of I$_2$ in ACOH until it produces a precipitation; The reaction mixture was concentrated in vacuo to provide a brown solid which was subjected to column chromatography (5% NH$_3$ sat'd MeOH/CH$_2$Cl$_2$) to provide 0.40 g (1.3 mmol, 35%) of the product.

1-Isopropyl-4-Iodo-5-(2-imidazolin-2-ylamino) benzimidazole. A reaction of the amine (0.40 g, 1.3 mmol) and ISA (0.5 g, 3.7 mmol) produced 0.18 g (0.48 mmol, 37%) of the product after chromatographic separation. The product obtained was converted to the fumarate salt and recrystallized from isopropanol to afford 0.22 g (35%) of the product as a white solid: mp 208–209° C.; Anal. Calc. for C$_{13}$H$_{16}$N$_5$I.1.0C$_4$H$_4$O$_4$ requires C, 42.05; H, 4.15; N, 14.43. Found: C, 41.86; H, 4.08; N, 14.17.

EXAMPLE 20

3-Isopropyl-5-(2-imidazolin-2-ylamino) benzimidazole. (#20).

A reaction of 3-isopropyl-5-aminobenzimidazole (1.0 g, 5.8 mmol) and ISA (1.5 g, 11 mmol) yielded 0.90 g (3.8 mmol, 65%) of product after column chromatography. The product obtained was converted to the fumarate salt and recrystallized from isopropanol to afford 0.32 g (25%) of the product as a light brown solid: mp 206–207° C.; Anal. Calc. for C$_{13}$H$_{17}$N$_5$0.5C$_4$H$_4$O, requires C, 54.67; H, 5.55; N, 16.78. Found: C, 53.33; H, 5.50; N, 16.30.

EXAMPLE 21

3-Isopropyl-4-bromo-5-(2-imidazolin-2-ylamino) benzimidazole (#21)

3-Isopropyl-4-bromo-5-aminobenzimidazole. To a solution of 3-isopropyl-5-aminobenzimidazole (1.5 g, 7.9 mmol)

in 20 ml of AcOH was added solution of Br. in AcOH until it produces a precipitation. The reaction mixture was concentrated in vacuo to provide a brown solid which was subjected to column chromatography (5% $NH_3$ sat'd MeOH/ $CH_2Cl_2$) to provide 1.1 g (4.0 mmol, 47%) of the product.

3-Isopropyl-4-bromo-5-(2-imidazolin-2-ylamino) benzimidazole. A reaction of 3-isopropyl-4-bromo-5-aminobenzimidazole (1.1 g, 4.0 mmol) and ISA (1.2 g, 9.0 mmol) provided 0.60 g (1.9 mmol, 43%) of product, after column chromatography. The product obtained was converted to the fumarate salt and recrystallized from EtOH to afford 0.52 g (28%) of the product as a white crystal: mp 210–212° C.; Anal. Calc. for $C_{13}H_{16}N_5Br.1.0C_4H_4O_4$ requires C, 46.59; H, 4.60; N, 15.98. Found: C, 46.60; H, 4.49; N, 15.74.

EXAMPLE 22

1-Isobutyl-5-(2-imidazolin-2-ylamino)benzimidazole (#22)

1- and 3-Isobutyl-5-aminobenzimidazole. A reaction of 5-nitrobenzimidazole (4.8 g, 29 mmol) and isobutyl bromide (7.7 ml, 72 mmol) in a procedure described in Example 9 produces 5.3 g (24 mmol, 83%) of a mixture of 1- and 3-isopropyl-5-nitrobenzimidazole, which was converted to the corresponding amines in hydrogenation ($H_2$/Pd-C). The amine mixture was subjected to column chromatography (10% i-PrOH/$CH_2Cl_2$) to provide 1.8 g (9.4 mmol, 32%) of 1-isobutyl-5-aminobenzimidazole and 2.7 g (14 mmol, 49%) of 3-isobutyl-5-aminobenzimidazole.

1-Isobutyl-5-(2-imidazolin-2-ylamino)benzimidazole. Reaction of 1-isobutyl-5-aminobenzimidazole (0.29 g, 1.2 mmol) and ISA (0.6 g, 4.5 mmol) provided 0.37 g (1.2 mmol, >95%) of the expected product after column chromatographic separation. The product obtained was converted to the fumarate salt and recrystallized from isopropanol to afford 0.41 g (70%) of the product as a white solid: mp 185–186° C.; Anal. Calc. for $C_{14}H_{19}N_5.2.0C_4H_4O_4$ requires C, 53.98; H, 5.56; N, 14.31. Found: C, 53.85; H, 5.69; N, 14.22.

EXAMPLE 23

1-Isobutyl-4-bromo-5-(2-imidazolin-2 ylamino) benzimidazole (#23)

1-Isobutyl-4-bromo-5-aminobenzimidazole. To a solution of 1-isobutyl-5-aminobenzimidazole (2.4 g, 13 mmol) in 20 ml of AcOH was added solution of $Br_2$ in AcOH until it produces a precipitation. The reaction mixture was concentrated in vacuo to provide a brown solid which was subjected to column chromatography (5% $NH_3$ sat'd MeOH/$CH_2Cl_2$) to provide 1.2 g (4.5 mmol, 35%) of the product.

1-Isobutyl-4-bromo-5-(2-imidazolin-2-ylamino) benzimidazole. A reaction of bromoamine (0.30 g, 1.1 mmol) and ISA (0.9 g, 6.7 mmol) produced 0.28 g (0.81 mmol, 73%;) of the product after chromatographic separation. The product obtained was converted to the fumarate salt and recrystallized from isopropanol to afford 0.28 g (56%) of the product as a white solid: mp 226–227° C.

EXAMPLE 24

3-Isobutyl-4-bromo-5-(2-imidazolin-2-ylamino) benzimidazole (#24)

3-Isobutyl-4-bromo-5-aminobenzimidazole. To a solution of 3-isobutyl-5-aminobenzimidazole (1.5 g, 7.9 mmol) in 20 ml of AcOH was added solution of $Br_2$ in AcOH until it produces a precipitation. The reaction mixture was concentrated in vacuo to provide a brown solid which was subjected to column chromatography (5% $NH_3$ sat'd MeOH/$CH_2Cl_2$) to provide 1.0 g (3.7 mmol, 29%) of the product.

3-Isobutyl-4-bromo-5-(2-imidazolin-2-ylamino) benzimidazole. A reaction of 3-isobutyl-4-bromo5-aminobenzimidazole (0.30 g, 1.1 mmol) and ISA (0.70 g, 5.2 mmol) provided 0.20 g (0.56 mmol, 51%) of the product after column chromatography. The product obtained was converted to the fumarate salt and recrystallized from isopropanol to afford 0.22 g (45%) of the product as a white solid: mp 187–188° C.; Anal. Calc. for $C_{14}H_{18}N_5Br.1.0C_4H_4O_4$ requires C, 47.80; H, 4.90; N, 15.48. Found: C, 47.57; H, 4.61; N, 15.38.

EXAMPLE 25

1-Cyclopentyl-5-(2-imidazolin-2-ylamino) benzimidazole (#25)

1- and 3-Cyclopentyl-5-aminobenzimidazole. A reaction of 5-nitrobenzimidazole (3.1 g, 19 mmol) and cyclopentyl bromide (3.8 ml, 38 mmol) in a procedure described in Example 9 produces 2.6 g (11 mmol, 59%) of a mixture of 1- and 3-cyclopentyl-B-nitrobenzimidazole, which was converted to the corresponding amines in hydrogenation ($H_2$/Pd-C). The amine mixture was subjected to column chromatography (10% i-PrOH/$CH_2Cl_2$) to provide 1.0 g (5.0 mmol, 45%) of 1-cyclopentyl-5-aminobenzimidazole and 1.1 g (5.4 mmol, 50%) of 3-cyclopentyl-5-aminobenzimidazole.

1-Cyclopentyl-5-(2-imidazolin-2-ylamino) benzimidazole. A reaction of 1-cyclopentyl-5-aminobenzimidazole (0.66 g, 3.3 mmol) and ISA (1.3 g, 9.7 mmol) provided 0.91 g (.7 mmol, 81%) of the expected product after column chromatographic separation. The product obtained was converted to the fumarate salt and recrystallized from isopropanol to afford 1.1 g (77%) of the product as a white crystal: mp 214–215° C.; Anal. Calc. for $C_{15}H_{19}N_5.1.5C_4H_4O_4$ requires C, 56.88; H, 5.68; N, 15.79. Found: C, 56.69; H, 5.54; N, 16.02.

EXAMPLE 26

1-Cyclopentyl-4-bromo-5-(2-imidazolin-2-ylamino) benzimidazole (#26)

1-Cyclopentyl-4-bromo-5-aminobenzimidazole. To a solution of 1-cyclopentyl-5-aminobenzimidazole (1.1 g, 5.5 mmol) in 20 ml of ACOH was added solution of $Br_2$ in. ACOH until it produces a precipitation. The reaction mixture was concentrated in vacuo to provide a brown solid which was subjected to column chromatography (5% $NH_3$ sat'd MeOH/$CH_2Cl_2$) to provide 0.54 g (1.9 mmol, 35%) of the product.

1-Cyclopentyl-4-bromo-5-(2-imidazolin-2-ylamino) benzimidazole. A reaction of the amine (0.54 g, 1.9 mmol) and ISA (0.74 g, 5.5 mmol) produced 0.45 g (1.3 mmol, 67%) of the product after chromatographic separation. The product obtained was converted to the fumarate salt and recrystallized from isopropanol to afford 0.32 g (19%) of the product as a light brown solid: mp 180–182° C.; Anal. Calc. for $C_{15}H_{18}N_5Br.1.5C_4H_4O_4$ requires C, 48.29; H, 4.63; N, 13.41. Found: C, 48.56; H, 4.54; N, 13.23.

EXAMPLE 27

3-Cyclopentyl-5-(2-imidazolin-2-ylamino) benzimidazole (#27).

A reaction of 3-cyclopentyl-5-aminobenzimidazole (0.41 g, 2.0 mmol) and ISA (0.68 g, 5.1 mmol) yielded 0.34 g (1.2 mmol, 62%) of product after column chromatography. The product obtained was converted to the fumarate salt and recrystallized from isopropanol to afford 0.28 g (31%) of the product as a white solid: mp 158–159° C.; Anal. Calc. for $C_{15}H_{19}N_5 \cdot 1.0 C_4H_{44}$ requires C, 56.88; H, 5.68; N, 15.79. Found: C, 55.69; H., 5.62; N, 15.73.

EXAMPLE 28

3-Cyclopentyl-4-bromo-5-(2-imidazolin-2 ylamino) benzimidazole (#28)

3-Cyclopentyl-4-bromo-5-aminobenzimidazole. To a solution of 3-cyclopentyl-5-aminobenzimidazole (1.0 g, 5.0 mmol) in 20 ml of AcOH was added solution of $Br_2$ in AcOH until it produces a precipitation. The reaction mixture was concentrated in vacuo to provide a brown solid which was subjected to column chromatography (5% $NH_3$ sat'd MeOH/$CH_2Cl_2$) to provide 0.70 g (2.5 mmol, 50%) of the product.

3-Cyclopentyl-4-bromo-5-(2-imidazolin-2-ylamino) benzimidazole. A reaction of 3-cyclopentyl-4-bromo-5-aminobenzimidazole (0.70 g, 2.5 mmol) and ISA (0.94 g, 7.0 mmol) provided 0.26 g (0.78 mmol, 31%) of product after column chromatography. The product obtained was converted to the fumarate salt and recrystallized from isopropanol to afford 0.31 g (27%) of the product as a white solid: mp 208–210° C.; Anal. Calc. for $C_{13}H_{19}N_5Br \cdot 1.0 C_4H_4O_4$ requires C, 49.15; H, 4.78; N, 15.08. Found: C, 49.46; H, 4.88; N, 15.38.

EXAMPLE 29

1-Cyclohexylmethyl-5-(2-imidazolin-2-ylamino) benzimidazole (#29)

1- and 3-Cyclohexylmethyl-5-aminobenzimidazole. A reaction of 5-nitrobenzimidazole (3.1 g, 19 mmol) and cyclohexylmethyl bromide (6.7 ml, 47 mmol) in a procedure described in Example 9 produces 5.0 g (19 mmol, 100%) of a mixture of 1- and 3-cyclohexylmethyl-5-nitrobenzimidazole, which was converted to the corresponding amines in hydrogenation ($H_2$/Pd-C). The amine mixture was subjected to column chromatography (10%–30% hexane/EtOAc) to provide 2.0 g (8.7 mmol, 45%) of 1-cyclohexylmethyl-5-aminobenzimidazole and 2.5 g (11 mmol, 54%) of 3-cyclohexylmethyl-5-aminobenzimidazole.

1-Cyclohexylmethyl-5-(2-imidazolin-2-ylamino) benzimidazole. A reaction of 1-cyclohexylmethyl-5-aminobenzimidazole (2.2 g, 9.6 mmol) and ISA (3.6 g) provided 1.8 g (8.1 mmol, 84%) of the expected product after column chromatographic separation. The product obtained was converted to the fumarate salt and recrystallized from isopropanol to afford 1.9 g (4.6 mmol, 48%) of the product as a white solid: mp 222–223° C.; Anal. Calc. for $C_{17}H_{23}N_5 \cdot 1.0 C_4H_4O_4$ requires C, 61.00; H, 6.58; N, 16.94. Found: C, 61.48; H, 6.41; N, 16.36.

EXAMPLE 30

1-Cyclohexylmethyl-4-bromo-5-(2-imidazolin-2-ylamino)benzimidazole (#30)

1-Cyclohexylmethyl-4-bromo-5-aminobenzimidazole. To a solution of 1-cyclohexylmethyl-5-aminobenzimidazole (2.5 g, 11 mmol) in 20 ml of AcOH was added solution of $Br_2$ in AcOH until it produces a precipitation. The reaction mixture was concentrated in vacuo to provide a brown solid which was subjected to column chromatography (5% $NH_3$ sat'd MeOH/$CH_2Cl_2$) to provide 1.37 g (4.3 mmol, 40%) of the product.

1-Cyclohexylmethyl-4-bromo-5-(2-imidazolin-2-ylamino)benzimidazole. A reaction of the amine (1.4 g, 4.4 mmol) and ISA (1.8 g, 13 mmol) produced 1.6 g (4.1 mmol, 94%) of the product after chromatographic separation. The product obtained was converted to the fumarate salt and recrystallized from isopropanol to afford 1.8 g (83%) of the product as a white solid: mp 193–195° C.; Anal. Calc. for $C_{17}H_{22}N_5Br \cdot 1.0 C_4H_4O_4$ requires C, 51.23; H, 5.32; N, 14.22. Found: C, 50.21; H, 5.17; N, 14.29.

EXAMPLE 31

3-Cyclohexylmethyl-4-bromo-5-(2-imidazolin-2-ylamino)benzimidazole (#31)

3-Cyclohexylmethyl-4-bromo-5-aminobenzimidazole. To a solution of 3-cyclohexylmethyl-5-aminobenzimidazole (2.0 g, 8.7 mmol) in 40 ml of AcOH was added solution of $Br_2$ in AcOH until it produces a precipitation. The reaction mixture was concentrated in vacuo to provide a brown solid which was subjected to column chromatography (5% $NH_3$ sat'd MeOH/$CHCl_3$) to provide 1.2 g (3.8 mmol, 48%) of the product.

3-Cyclohexylmethyl-4-bromo-5-(2-imidazolin-2-ylamino)benzimidazole. A reaction of 3-cyclohexylmethyl4-bromo-5-aminobenzimidazole (1.2 g, 3.9 mmol) and ISA (1.5 g, 11 mmol) provided 0.85 g (2.3 mmol, 58%) of product after column chromatography. The product obtained was converted to the fumarate salt and recrystallized from isopropanol to afford 1.1 g (51%) of the product as a white solid: mp 153–155° C.; Anal. Calc. for $C_{17}H_{22}N_5Br \cdot 1.5 C_4H_4O \cdot 0.5 H_2O$ requires C, 49.38; H, 5.22; N, 12.58. Found: C, 49.22; H, 5.07; N, 12.19.

EXAMPLE 32

1-Benzyl-5-(2-imidazolin-2-ylamino)benzimidazole (#32)

1- and 3-Benzyl-5-aminobenzimidazole. A reaction of 5-nitrobenzimidazole (3.0 g, 18 mmol) and benzyl bromide (4.4 ml, 37 mmol) in a procedure described in Example 9 produces 3.2 g (13 mmol, 71%) of a mixture of 1- and 3-benzyl-5-nitrobenzimidazole, which was converted to the corresponding amines in hydrogenation ($H_2$/Pd-C). The amine mixture was subjected to column chromatography (10%–30% Hexane/EtOAc) to provide 1.6 g (7.2 mmol, 55%) of 1-benzyl-5-aminobenzimidazole and 1.2 g (5.3 mmol, 41%) of 3-benzyl-5-aminobenzimidazole.

1-benzyl-5-(2-imidazolin-2-ylamino)benzimidazole. A reaction of 1-benzyl-5-aminobenzimidazole (0.35 g, 1.2 mmol) and ISA (0.42 g, 3.1 mmol) provided 0.17 g (0.46 mmol, 38%) of the expected product after column chromatographic separation. The product obtained was converted to the fumarate salt and recrystallized from isopropanol to afford 0.11 g (20%) of the product as a white solid: mp 174–175° C.; Anal. Calc. for $C_{17}H_{17}N_5 \cdot 1.5 C_4H_4O_4$ requires C, 59.35; H, 4.98; N, 45.05. Found: C, 59.40; H, 4.81; N, 14.99.

EXAMPLE 33

1-Benzyl-4-bromo-5-(2-imidazolin-2-ylamino) benzimidazole (#33)

1-Benzyl-4-bromo-5-aminobenzimidazole. To a solution of 1-benzyl-5-aminobenzimidazole (1.0 g, 5.0 mmol) in 40 ml of AcOH was added solution of $Br_2$ in AcOH until it produces a precipitate. The reaction mixture was concentrated in vacuo to provide a brown solid which was subjected to column chromatography (5% $NH_3$ sat'd $MeOH/CHCl_3$) to provide 0.90 g (2.5 mmol, 60%) of the product.

1-Benzyl-4-bromo-5-(2-imidazolin-2-ylamino) benzimidazole. A reaction of bromoamine,(0.90 g, 3.0 mmol) and ISA (1.2 g, 8.9 mmol) produced 0.85 g (2.3 mmol, 77%) of the product after chromatographic separation. The product obtained was converted to the fumarate salt and recrystallized from isopropanol to afford 1.1 g (70%) of the product as a white solid: mp 197–198° C.; Anal. Calc. for $C_{17}H_{16}N_5Br.1.5C_4H_4O_4$ requires C, 50.75; H, 4.07; N, 12.87. Found: C, 50.91; H, 3.67; N, 12.77.

EXAMPLE 34

3-Benzyl-5-(2-imidazolin-2-ylamino)benzimidazole (#34).

A reaction of 3-benzyl-5-aminobenzimidazole (0.34 g, 1.6 mmol) and ISA (0.68 g, 5.1 mmol) yielded 0.43 g (1.3 mmol, 76%) of product after column chromatography. The product obtained was converted to the fumarate salt and recrystallized from isopropanol to afford 0.329 g (41%) of the product as a white solid: mp 174–175° C.; Anal. Calc. for $C_{17}H_{17}N_5.1.5C_4H_4O_4$ requires C, 59.35; H, 4.98; N, 15.05. Found: C, 58.88; H, 5.19; N, 15.25.

EXAMPLE 35

3-benzyl-4-bromo-5-(2-imidazolin-2-ylamino) benzimidazole (#35)

3-Benzyl-4-bromo-5-aminobenzimidazole. To a solution of 3-benzyl-5-aminobenzimidazole (0.88 g, 3.9 mmol) in 20 ml of AcOH was added solution of $Br_2$ in ACOH until it produces a precipitation. The reaction mixture was concentrated in vacuo to provide a brown solid which was subjected to column chromatography (5% $NH_3$ sat'd $MeOH/CHCl_3$) to provide 0.35 g (1.2 mmol, 29%) of the product.

3-Benzyl-4-bromo-5-(2-imidazolin-2-ylamino) benzimidazole. A reaction of 3-benzyl-4-bromo-5-aminobenzimidazole (0.35 g, 1.2 mmol) and ISA (0.43 g, 3.2 mmol) provided 0.17 g (0.46 mmol, 38%) of the product after column chromatography. The product obtained was converted to the fumarate salt and recrystallized from MeOH to afford 0.12 g (21%) of the product as a white solid: mp 203–205° C.; Anal. Calc. for $C_{17}H_{16}N_5Br.1.0C_4H_4O_4$ requires C, 51.87; H, 4.64; N, 14.39. Found: C, 52.60; H, 4.73; N, 14.39.

EXAMPLE 36

1-(4-Methoxybenzyl)-4-bromo-5-(2-imidazolin-2-ylamino)benzimidazole (#36)

1-(4-Methoxybenzyl)-5-aminobenzimidazole. A reaction of 5-nitrobenzimidazole (4.3 g, 27 mmol) and 4-methoxybenzyl chloride (4.3 ml, 30 mmol) in a procedure described in Example 9 produces 5.6 g (19 mmol, 73%) of a mixture of 1- and 3-(4-methoxybenzyl)-5-nitrobenzimidazole, which was converted to the corresponding amines in hydrogenation ($H_2/Pd-C$). The amine mixture was subjected to column chromatography (10%–30% i-PrOH/$CH_2Cl_2$) to provide 2.1 g (8.2 mmol, 43%) of 1-(4-methoxybenzyl)-5-aminobenzimidazole and 2.4 g (9.2 mmol, 48%) of 3-(4-methoxybenzyl)-5-aminobenzimidazole.

1-(4-Methoxybenzyl)-4-bromo-5-aminobenzimidazole. To a solution of 1-(4-methoxybenzyl)-5-aminobenzimidazole (0.80 g, 2.2 mmol) in 20 ml of AcOH was added solution of $Br_2$ in AcOH until it produces a precipitation. The reaction mixture was concentrated in vacuo to provide a brown solid which was subjected to column chromatography (5% $NH_3$ sat'd $MeOH/CHCl_3$) to provide 0.90 g (2.1 mmol, 95%) of the product.

1-(4-Methoxybenzyl)-4-bromo-5-(2-imidazolin-2-ylamino)benzimidazole. A reaction of the bromoamine (0.90 g, 2.1 mmol) and ISA (1.3 g, 9.7 mmol) provided 1.0 g (2.0 mmol, 96%) of the product after column chromatography.

EXAMPLE 37

1-(3-Methoxybenzyl)-4-bromo-5-(2-imidazolin-2-ylamino)benzimidazole (#37)

1-(3-Methoxybenzyl)-5-aminobenzimidazole. A reaction of 5-nitrobenzimidazole (2.5 g, 15 mmol) and 3-methoxybenzyl chloride (2.6 ml, 17 mmol) in a procedure described in Example 9 produces 1.0 g (3.1 mmol, 26%) of a mixture of 1- and 3-(3-methoxybenzyl)-5-nitrobenzimidazole, which was converted to the corresponding amines in hydrogenation ($H_2/Pd-C$). The amine mixture was subjected to column chromatography (10%–30% isopropanol/$CH_2Cl_2$) to provide 0.32 g (1.1 mmol, 36%) of 3-(3-methoxybenzyl)-5-aminobenzimidazole and 0.37 g (1.3 mmol, 41%) of 1-(3-methoxybenzyl)-5-aminobenzimidazole.

1-(3-Methoxybenzyl)-4-bromo-5-aminobenzimidazole. To a solution of 1-(3-methoxybenzyl)-5-aminobenzimidazole (0.37 g, 1.3 mmol) in 10 ml of AcOH was added solution of $Br_2$ in AcOH until it produces a precipitation. The reaction mixture was concentrated in vacuo to provide a brown solid which was subjected to column chromatography (5% $NH_3$ sat'd Isopropanol/ $CHCl_3$) to provide 0.31 g (1.0 mmol, 66%) of the product.

1-(3-Methoxybenzyl)-4-bromo-5-(2-imidazolin-2-ylamino)benzimidazole. A reaction of the bromoamine (0.31 g, 0.84 mmol) and ISA (0.52 g, 3.9 mmol) provided 0.37 g (>95%) of product after column chromatography. The product obtained was converted to the fumarate salt and recrystallized from isopropanol to afford 0.36 g (83%) of the product as a white crystal: mp 177–178° C.; Anal. Calc. for $C_{18}H_{18}N_5BrO.1.0C_4H_4O_4.H_2O$ requires C, 48.63; H, 4.64; N, 12.89. Found: C, 48.06; H, 4.51; N, 12.77.

EXAMPLE 38

1-(2-Hydroxyethyl)-4-bromo-5-(2-imidazolin-2-ylamino)benzimidazole (#38) 1- and 3-(2-Hydroxyethyl)-4-bromo-5-aminobenzimidazole.

A reaction of 5-nitrobenzimidazole (3.3 g, 20 mmol) and 2-hydroxyethyl bromide (2.2 ml, 31 mmol) in a procedure described in Example 9 produces a mixture of 1- and 3-(2-hydroxyethyl)-5-nitrobenzimidazole, which was converted to the corresponding amines in hydrogenation ($H_2/$ Pd-C). The amine mixture (3.4 g, 19 mmol) in 50 ml of AcOH was added solution of $Br_2$ in AcOH until it produces a precipitation. The reaction mixture was concentrated in vacuo to provide a brown solid which was subjected to column chromatography (5% $NH_3$ sat'd isopropanol/ $CHCl_3$) to provide 0.42 g (1.6 mmol) of 3-(2-hydroxyethyl)-4-bromo-5-aminobenzimidazole and 0.57 g (2.2 mmol, 11%) of 1-(2-hydroxyethyl)-4-bromo-5-aminobenzimidazole.

1-(2-Hydroxyethyl)-4-bromo-5-(2-imidazolin-2-ylamino)benzimidazole. A reaction of 1-(2-hydroxyethyl)-

4-bromo-5-aminobenzimidazole (0.25 g, 1.4 mmol) and ISA (0.35 g, 2.6 mmol) provided 0.21 g (0.87 mmol, 62%) of product after column chromatography. The product obtained was converted to the fumarate salt and recrystallized from isopropanol to afford 0.17 g (28%) of the product as a white solid: mp 141–143° C.; Anal. Calc. for $C_{12}H_{14}N_5OBr.1.0C_4H_4O_4$ requires C, 43.55; H, 4.12; N, 15.87. Found: C, 44.14; H, 4.03; N, 15.53.

EXAMPLE 39

3-(2-Hydroxyethyl)-4-bromo-5-(2-imidazolin-2-ylamino)benzimidazole (#39)

A reaction of 3-(2-hydroxy-1-ethyl)-4-bromo-5-aminobenzimidazole (0.31 g, 1.8 mmol) and ISA (0.52 g, 3.9 mmol) provided 0.37 g (1.6 mmol, 88%) of the desired product after column chromatography. The product obtained was converted to the fumarate salt and recrystallized from isopropanol to afford 0.32 g (40%) of the product as a white solid: mp 217–218° C.

EXAMPLE 40

1-(2-Aminoethyl)-4-bromo-5-(2-imidazolin-2-ylamino)benzimidazole (#40)

To a solution of 1-(2-hydroxyethyl)-5-nitrobenzimidazole (0.27 g, 1.3 mmol) was added triphenylphosphine (0.38 g, 1.4 mmol), DEAD (0.25 ml, 1.4 mmol) and phthalimide (0.21 g, 1.4 mmol) in a portion and resulting mixture was stirred for 1 h at 25° C. The reaction mixture was concentrated in vacuo, yielding an oil which was subjected to column chromatography (40% Hexane/EtOAc) to provide 0.36 g (1.1 mmol, 82%) of 1-(2-phthalimidylethyl)-5-nitrobenzimidazole. The nitrobenzimidazole was subsequently subjected to hydrogenation, bromination and coupling with ISA to produce 0.41 g of 1-(2-phthalimidylethyl)-4-bromo-5-(2-imidazolin-2-ylamino)benzimidazole which was refluxed with 0.3 ml of hydrazine in 20 ml of MeOH for 0.5 h to yield the desired product (0.31 g, 0.96 mmol, 68% overall). The product obtained was converted to the fumarate salt and recrystallized from isopropanol to afford 0.21 g (24%) of the product as a white foamy solid.

EXAMPLE 41

2-Methyl-5-(2-imidazolin-2-ylamino)benzimidazole (#41)

2-Methyl-5-aminobenzimidazole. A solution of 4-nitro-1,2-phenylenediamine (1.0 g, 6.5 mmol) in 20 ml of AcOH was stirred at ref lux for 12 h. Reaction mixture was concentrated in vacuo to yield a dark brown residue, which, in spectroscopic analysis, corresponds to 2-methyl-5-nitrobenzimidazole and was subjected to a following reaction without further purification. The nitrobenzimidazole and 50 mg of 10% Pd/C were dissolved in 100 ml of MeOH and stirred for 12 h under $H_2$. The reaction mixture was filtered and concentrated in vacuo yielding 0.95 g (6.5 mmol, >95%) of brown oil which was identified as 2-methyl-5-aminobenzimidazole in NMR and used in a following reaction without further purification.

2-Methyl-5-(2-imidazolin-2-ylamino)benzimidazole. A solution of the amine (0.70 g, 4.7 mmol) and ISA (0.8 g, 5.9 mmol) was stirred at reflux for 12 h. The reaction mixture was concentrated in vacuo to yield an oily residue which was subjected to silica gel column chromatography ($NH_3$ sat'd 20% MeOHl/EtOAc) to yield 0.81 g (3.8 mmol, 81%) of the desired product.

EXAMPLE 42

2-Methyl-4-bromo-5-(2-imidazolin-2-ylamino)benzimidazole (#42)

2-Methyl-4-bromo-5-aminobenzimidazole. To a solution of 0.9 g (6.1 mmol) of 2-methyl-5-aminobenzimidazole in 50 ml of AcOH was added 0.16 ml of $Br_2$ (3.1 mmol) dropwise and resulting reaction mixture was stirred for 1 h at 25° C. Reaction mixture was concentrated in vacuo and purified on silica gel column chromatography (20% Isopropanol/EtOAC) to yield 0.56 g (2.5 mmol, 41%) of the desired product.

2-Methyl-4-bromo-5-(2-imidazolin-2-ylamino)benzimidazole. The amine (0.56 g, 2.5 mmol) and ISA (1.0 g, 7.4 mmol) were dissolved in 5 ml of isobutanol and stirred at reflux for 12 h. The reaction mixture was concentrated in vacuo and subjected to column chromatography ($NH_3$ sat'd 20% Isopropanol/EtOAC) to yield 0.72 g (2.4 mmol, >99%) of the product. The product obtained was converted to the fumarate salt and recrystallized from MeOH to afford 0.25 g (25%) of the product as a white crystal: mp 222–224° C.; Anal. Calc. for $C_{11}H_{12}N_5Br.1.0C_4H_4O_4.0.5H_2O$ requires C, 42.98; H, 4.09; N, 16.71. Found: C, 43.14; H, 4.03; N, 16.33.

EXAMPLE 43

2-Ethyl-4-bromo-5-(2-imidazolin-2-ylamino)benzimidazole (#43)

2-Ethyl-5-aminobenzimidazole. A solution of 4-nitro-1,2-phenylenediamine (1.0 g, 6.5 mmol) in 20 ml of propionic acid was stirred at ref lux for 12 h. Reaction mixture was concentrated in vacuo to yield a dark brown residue, which, in spectroscopic analysis, corresponds to 2-ethyl-5-nitrobenzimidazole and was subjected to a following reaction without further purification. The nitrobenzimidazole and 50 mg of 10% Pd-C were dissolved in 100 ml of MeOH and stirred for 12 h under $H_2$. The reaction mixture was filtered and concentrated in vacuo yielding 0.95 g (6.5 mmol, >95%) of brown oil which was identified as 2-ethyl-5-aminobenzimidazole in NMR and used in a following reaction without further purification.

2-Ethyl-4-bromo-5-aminobenzimidazole. To a solution of 1.3 g (7.7 mmol) of 2-ethyl-5-aminobenzimidazole in 50 ml of AcOH was added 0.40 ml of $Br_2$ (7.5 mmol) dropwise and resulting reaction mixture was stirred for 1 h at 25° C. The reaction mixture was concentrated in vacuo and purified on silica gel column chromatography (20% isopropanol /EtOAC) to yield 1.5 g (6.3 mmol, 82%) of the desired product.

2-Ethyl-4-bromo-5-(2-imidazolin-2-ylamino)benzimidazole.

A reaction of 2-ethyl-4-bromo-5-aminobenzimidazole (1.5 g, 6.3 mmol) with ISA (2.3 g, 17 mmol) provides 1.4 g (4.5 mmol, 71%) of the desired product. The product obtained was converted to the fumarate salt and recrystallized from isopropanol to afford 1.53 g (61%) of the product as a white solid: mp 186–187° C.; Anal. Calc. for $C_{12}H_{14}N_5Br.1.0C_4H_4O_4$ requires C, 45.30; H, 4.28; N, 16.51. Found: C, 45.03; H, 4.11; N, 16.88.

EXAMPLE 44

2-Isopropyl-4-bromo-5-(2-imidazolin-2-ylamino)benzimidazole (#44)

2-Isopropyl-5-aminobenzimidazole. A solution of 4-nitro-1,2-phenylenediamine (0.9 g, 5.9 mmol) in 5 ml of isobutyric acid was stirred at reflux for 12 h. The reaction mixture was concentrated in vacuo to yield a dark brown residue, which was dissolved in 100 ml of EtOAc and washed with aqueous NaHCO$_3$. Organic layer was dried over MgSO$_4$ and concentrated in vacuo, yielding an oil which was characterized as 2-isopropyl-5-nitrobenzimidazole and subjected to a following reaction without further purification. The nitrobenzimidazole and 50 mg of 10% Pd-C were dissolved in 100 ml of MeOH and stirred for 12 h under H$_2$. The reaction mixture was filtered and concentrated in vacuo, yielding 0.95 g (5.4 mmol, 92%) of the desired product.

2-Isopropyl-4-bromo-5-aminobenzimidazole. To a solution of 0.95 g (5.4 mmol) of 2-isopropyl-5-aminobenzimidazole in 50 ml of ACOH was added 0.19 ml (3.7 mmol) of Br$_2$ dropwise and resulting reaction mixture was stirred for 1 h at 25° C. Reaction mixture was concentrated in vacuo and purified on silica gel column chromatography (5% MeOH/EtOAC) to yield 0.89 g (3.5 mmol, 95%) of the desired product.

2-Isopropyl-4-bromo-5-(2-imidazolin-2-ylamino) benzimidazole. A reaction of the bromoamine (0.89 g, 3.5 mmol) and ISA (1.5 g, 11 mmol) provides 0.42 g (1.3 mmol, 37%) of the expected product. The product obtained was converted to the fumarate salt and recrystallized from EtOH to afford 0.43 g (28%) of the product as a light gray solid: mp 176–178° C.; Anal. Calc. for $C_{13}H_{16}N_5Br \cdot 1.0C_4H_4O_4$ requires C, 46.59; H, 4.60; N, 15.98. Found: C, 45.14; H, 4.39; N, 15.78;

EXAMPLE 45

2-tert-Butyl-4-bromo-5-(2-imidazolin-2-ylamino) benzimidazole (#45)

2-tert-Butyl-5-aminobenzimidazole. A solution of 4-nitro-1,2-phenylenediamine (2.0 g, 13 mmol) in 10 ml of trimethylacetic acid was stirred at reflux for 12 h. Reaction mixture was concentrated in vacuo to yield a oil which was subjected to column chromatography (CHCl$_3$, neat) to yield 2.2 g (10 mmol, 77%) of 2-tert-butyl-5-nitrobenzimidazole. The nitrobenzimidazole and 0.5 g of 10% Pd-C were dissolved in 100 ml of MeOH and stirred for 12 h under H$_2$. The reaction mixture was filtered and concentrated in vacuo to provide 1.9 g (10 mmol, >95%) of the desired product.

2-tert-Butyl-4-bromo-5-aminobenzimidazole . To a solution of 0.53 g (2.8 mmol) of 2-tert-butyl-5-aminobenzimidazole in 50 ml of AcOH was added 0.05 ml (1.0 mmol) of Br$_2$ dropwise and resulting reaction mixture was stirred for 1 h at 25° C. Reaction mixture was concentrated in vacuo and purified on silica gel column chromatography (CHCl$_3$, neat) to yield 0.18 g (0.67 mmol, 67%) of the desired product.

2-tert-Butyl-4-bromo-5-(2-imidazolin-2-ylamino) benzimidazole. A reaction of the bromoamine (0.18 g, 0.67 mmol) and ISA (0.30 g, 2.2 mmol) provides 0.21 g (0.62 mmol, 93%) of the product. The product obtained was converted to the fumarate salt and recrystallized from EtOH to afford 0.43 g (28%) of the product as a light gray solid: mp 176–178° C.; Anal. Calc. for $C_{14}H_{18}N_5Br \cdot 1.0C_4H_4O_4$ requires C, 47.48; H, 4.90; N, 15.48. Found: C, 45.14; H, 4.39; N, 15.78.

EXAMPLE 46

2-Trifluoromethyl-4-bromo-5-(2-imidazolin-2-ylamino)benzimidazole (#46)

2-Trifluoromethyl-5-aminobenzimidazole. A solution of 4-nitro-1,2-phenylenediamine (3.0 g, 20 mmol) in 15 ml of trifluoroacetic acid was stirred at reflux for 12 h. The reaction mixture was concentrated in vacuo to yield a oily residue, which was dissolved in 100 ml of EtOAc and washed with aqueous NaHCO$_3$. The organic layer was dried over MgSO$_4$ and concentrated in vacuo to provide an oil which was characterized as 2-trifluoromethyl-5-nitrobenzimidazole and subjected to the following reaction without further purification. The nitrobenzimidazole and 500 mg of 10% Pd-C were dissolved in 100 ml of MeOH and stirred for 12 h under H$_2$. The reaction mixture was filtered and concentrated in vacuo, yielding 3.2 g (16 mmol, 80%) of the desired product.

2-Trifluoromethyl-4-bromo-5-aminobenzimidazole. To a solution of 3.2 g (16 mmol) of 2-trifluoromethyl-5-aminobenzimidazole in 50 ml of AcOH was added 0.34 ml (6.6 mmol) of Br$_2$ dropwise and resulting reaction mixture was stirred for 1 h at 25° C. The reaction mixture was concentrated in vacuo and purified on silica gel column chromatography (10% MeOH/CHCl$_3$) to yield 1.7 g (6.2 mmol, 94%) of the desired product.

2-Trifluoromethyl-4-bromo-5-(2-imidazolin -2-ylamino) benzimidazole. Reaction of the bromoamine (1.3 g, 4.6 mmol) and ISA (1.5 g) provided 0.39 g (1.1 mmol, 23%) of the desired product. The product obtained was converted to the fumarate salt and recrystallized from EtOH to afford 0.40 g (21%) of the product as a light brown solid: mp 231–232° C.

EXAMPLE 47

2-Cyclopropyl-4-bromo-5-(2-imidazolin-2-ylamino) benzimidazole (#47)

2-Cyclopropyl-5-aminobenzimidazole. A solution of 4-nitro-1,2-phenylenediamine (1.0 g, 6.6 mmol) in 15 ml of cyclopropanecarboxylic acid was stirred at reflux for 12 h. The reaction mixture was concentrated in vacuo to yield a oil, which was dissolved in 100 ml of EtOAc and washed with aqueous NaHCO$_3$. Organic layer was dried over MgSO$_4$ and concentrated in vacuo, yielding an oil which was characterized as 2-cyclopropyl-5-nitrobenzimidazole and subjected to a following reaction without further purification. The nitrobenzimidazole and 50 mg of 10% Pd-C were dissolved in 100 ml of MeOH and stirred for 12 h under H$_2$. The reaction mixture was filtered and concentrated in vacuo to provide 0.87 g (4.9 mmol, 75%) of the desired product.

2-Cyclopropyl-4-bromo-5-aminobenzimidazole. To a solution of 0.87 g (4.9 mmol) of 2-cyclopropyl-5-aminobenzimidazole in 50 ml of AcOH was added 0.10 ml (1.9 mmol) of Br$_2$ dropwise and resulting reaction mixture was stirred for 1 h at 25° C. The reaction mixture was concentrated in vacuo and purified on silica gel column chromatography (5% MeOH/EtOAC) to yield 0.42 g (1.8 mmol, >95%) of the desired product.

2-Cyclopropyl-4-bromo-5-(2-imidazolin-2-ylamino) benzimidazole. A reaction of the bromoamine (0.69 g, 2.4 mmol) and ISA (1.1 g, 8.2 mmol) provides 0.71 g (2.2 mmol, 92%) of the desired product. The product obtained was converted to the fumarate salt and recrystallized from isobutanol to afford 0.62 g (62%) of the product as a light yellow solid: mp 81–83° C.; Anal. Calc. for $C_{12}H_{14}N_5Br \cdot 1.0C_4H_4O_4 \cdot 1.0H_2O$ requires C, 44.95; H, 4.44; N, 15.42. Found: C, 45.28; H, 4.35; N, 14.94.

EXAMPLE 48

2-Diphenylmethyl-4-bromo-5-(2-imidazolin-2-ylamino)benzimidazole (#48)

2-Diphenylmethyl-5-aminobenzimidazole. A solution of 4-nitro-1,2-phenylenediamine (2 g, 13 mmol) in 10 g of diphenylacetic acid(neat) was stirred at reflux for 12 h. Reaction mixture was concentrated In Vacuo to yield a dark brown residue, which was dissolved in 100 ml of EtOAc and washed with aqueous $NaHCO_3$. Organic layer was dried over $MgSO_4$ and concentrated in vacuo, yielding an oil which was purified on column chromatography (50% Hexane/EtOAc) to yield 1.7 g (5.3 mmol, 39%) of 2-diphenylmethyl-5-nitrobenzimidazole. The nitrobenzimidazole and 250 mg of 10% Pd-C were dissolved in 100 ml of MeOH and stirred for 12 h under $H_2$. The reaction mixture was filtered and concentrated in vacuo to provide 1.4 g (5.2 mmol, >95%) of the desired product.

2-Diphenylmethyl-4-bromo-5-aminobenzimidazole. To a solution of 1.1 g (3.7 mmol) of 2-diphenylmethyl-5-aminobenzimidazole in 50 ml of AcOH was added 0.07 ml (1.3 mmol) of $Br_2$ dropwise and resulting reaction mixture was stirred for 1 h at 25° C. Reaction mixture was concentrated in vacuo and purified on silica gel column chromatography (5% MeOH/EtOAC) to yield 0.42 g (1.1 mmol, 86%) of the desired product.

2-Diphenylmethyl-4-bromo-5-(2-imidazolin-2-ylamino) benzimidazole. A reaction of the amine (1.1 g, 2.9 mmol) and ISA (1.5 g, 11 mmol) produces 0.51 g (1.1 mmol, 39%) of the expected product. The product obtained was converted to the fumarate salt and recrystallized from MeOH to afford 0.31 g (21%) of the product as a light brown solid: mp 240–242° C.; Anal. Calc. for $C_{23}H_{20}N_5Br.1.0C_4H_4O_4$ requires C, 57.66; H, 4.30; N, 12.45. Found: C, 57.58; H. 4.12; N, 12.28.

EXAMPLE 49

6-Methyl-5-(2-imidazolin-2-ylamino)benzimidazole (#49)

6-Methyl-5-aminobenzimidazole. To a solution of 20 ml of fuming nitric acid was added 5-methylbenzimidazole (1.6 g, 12 mmol) slowly over 0.5 h and reaction mixture was stirred for 3 h at −15° C. During addition of substrate, reaction temperature was kept below −10° C. Sticky reaction mixture was then poured into ice water to form a yellow precipitation, which was collected and dried in vacuo to provide 0.37 g (2.1 mmol, 17%) of 5-methyl-6-nitrobenzimidazole. The nitrobenzimidazole was converted to the corresponding amine (0.32 g, 95%) on hydrogenation ($H_2$, Pd/C).

6-Methyl-5-(2-imidazolin-2-ylamino)benzimidazole. The amine obtained above was stirred at reflux with ISA (0.96 g, 7.2 mmol) in isobutanol for 12 h. Column chromatographic separation of reaction mixture ($NH_3$ sat'd 30% MeOH/EtOAc) produced 0.40 g (1.6 mmol, 78%) of the desired product. The product obtained was converted to the fumarate salt and recrystallized from EtOH to afford 0.43 g (63%) of the product as a white solid: mp 219–221° C.; Anal. Calc. for $C_{11}H_{13}N_5.1.0C_4H_4O_4$ requires C, 54.38; H, 5.17; N, 21.14. Found: C, 54.14; H, 5.33; N, 20.84.

EXAMPLE 50

4,6-Dibromo-5-(2-imidazolin-2-ylamino) benzimidazole (#50).

To a solution of 4-bromo-5-(2-imidazolin-2-ylamino) benzimidazole (0.2 g, 0.7 mmol) in 10 ml AcOH was added 200 mg of $Hg(OAc)_2$ and few drops of $Br_2$. Reaction mixture was concentrated in vacuo, yielding a dark oily residue, which was subjected to silica gel column chromatography ($NH_3$ sat'd 30% MeOH/EtOAc) to provide 210 mg (0.58 mmol, 86%) of the desired product. The product obtained was converted to the fumarate salt and recrystallized from EtOH to afford 0.051 g (14%) of the product as a white solid.

EXAMPLE 51

7-Bromo-5-(2-imidazolin-2-ylamino)benzimidazole (#51)

2,4-Dinitro-6-bromoaniline. To a solution of 2,4-dinitroaniline (2.2 g, 12 mmol) in 40 ml of ACOH was added 1.0 ml of $Br_2$ dropwise and reaction mixture was stirred for 1 h. The reaction mixture was concentrated in vacuo, yielding a dark residue which was diluted with EtOAc and washed with aqueous $NaHCO_3$. Organic layer was dried over $MgSO_4$ and concentrated in vacuo to provide 2.9 g (11 mmol, 92%) of 2,4-dinitro-6-bromo-aniline which was characterized by NMR and used in a following reaction without further purification.

4-Bromo-6-aminobenzimidazole. A solution of 4.0 g of $SnCl_2.2H_2O$ and 15 ml of HCl was added into 2,4-dinitro-6-bromoaniline (1.8 g, 6.9 mmol) and resulting reaction mixture was stirred for 2 h at 25° C. The reaction mixture was then basified by adding 15% aq. NaOH and extracted with $CHCl_3$ several times. Combined extracts were dried over $MgSO_4$ and concentrated in vacuo to produce 1.4 g (>95%) of corresponding amine. The amine was stirred at reflux in 10 ml of formic acid and 10 ml of acetic anhydride for 12 h. The reaction mixture was concentrated in vacuo, yielding oily residue which was stirred in 30 ml of HCl sat'd EtOH for 0.5 h. The oily reaction mixture after concentration was subjected to column chromatography (5% $NH_3$ sat'd MeOH/EtOAc) to yield 1.3 g (>95%) of the desired product.

7-Bromo-5-(2-imidazolin-2-ylamino)benzimidazole. 4-bromo-6-aminobenzimidazole (0.4 g, 1.9 mmol) and ISA (1.2 g, 8.9 mmol) was dissolved in isobutanol and stirred at reflux for 12 h. Column chromatographic separation of the reaction mixture ($NH_3$ sat'd 20% MeOH/EtOAc) provided 0.41 g (1.5 mmol, 78%) of the product. The product obtained was converted to the fumarate salt and recrystallized from isopropanol to afford 0.24 g (32%) of the product as a light brown solid: mp 217–218° C.; Anal. Calc. for $C_{10}H_{10}N_5Br.1.0C_4H_4O_4$ requires C, 42.44; H, 3.56; N, 17.68. Found: C, 42.28; H. 3.58; N, 17.40.

EXAMPLE 52

7-Methyl-5-(2-imidazolin-2-ylamino)benzimidazole (#52)

4-Methyl-6-aminobenzimidazole. To the solution of 4-bromo-6-aminobenzimidazole (0.85 g, 6.0 mmol) in sealed tube with 10 ml of DMF was added tetramethyltin (1.7 ml, 12 mmol) and bis(triphenylphosphine)palladium(II) chloride (0.20 g). The resulting reaction mixture was stirred for 12 h at 140° C. and concentrated in vacuo, yielding oily residue which was subjected to column chromatography (5% $MeOH/CHCl_3$)to produce 0.28 g (45%) of the desired product.

7-Methyl-5-(2-imidazolin-2-ylamino)benzimidazole. A solution of the amine (0.28 g, 1.8 mmol) and ISA (0.82 g, 6.2 mmol) was stirred at reflux for 24 h. The reaction mixture was subjected to column chromatography (30% $NH_3$ sat'd MeOH/EtOAc) to yield 0.23 g (57%) of the product. The product obtained was converted to the fumarate salt and recrystallized from isopropanol to afford 0.24 g (40%) of the product as a light brown solid: mp 229–231° C.; Anal. Calc.

EXAMPLE 53

7-Chloro-5-(2-imidazolin-2-ylamino)benzimidazole (#53)

4-chloro-6-aminobenzimidazole. Methanolic solution of 6-chloro-2,4-dinitroaniline (2.4 g, 11 mmol) was stirred overnight with 100 mg of 10% Pd/C under $H_2$. Reaction mixture was filtered and concentrated in vacuo to provide an oil which was dissolved in 10 ml of acetic anhydride and 10 ml of formic acid and stirred at reflux for 12 h. The reaction mixture was concentrated in vacuo, yielding a brown oil which was characterized as 4-chloro-6-foramidylbenzimidazole in NMR analysis. The foramide was dissolved in 20 ml of HCl sat'd EtOH and stirred for 3 h at 25° C. The reaction mixture was purified in column chromatography (5% MeOH/EtOAc) to provide 0.89 g (5.3 mmol, 48% overall) of the desired product.

7-Chloro-5-(2-imidazolin-2-ylamino)benzimidazole. A solution of 4-chloro-6-aminobenzimidazole (0.9 g, 5.4 mmol) and ISA (1.7 g, 13 mmol) was stirred at reflux for 24 h. Column chromatographic separation of reaction mixture (30% $NH_3$ sat'd MeOH/EtOAc) provided 0.53 g (2.2 mmol, 41%) of the product. The product obtained was converted to the fumarate salt and recrystallized from MeOH to afford 0.41 g (22%) of the product as a light brown solid: mp 220–221° C.; Anal. Calc. for $C_{10}H_{10}N_5Cl.1.0C_4H_4O_4$ requires C, 47.81; H, 4.01; N, 19.91. Found: C, 46.03; H, 4.14; N, 19.64.

EXAMPLE 54

7-Iodo-5-(2-imidazolin-2-ylamino)benzimidazole (#54)

2,4-Dinitro-6-iodoaniline. To a solution of 2,4-dinitroaniline (3.0 g, 16 mmol) and $Hg(OAc)_2$ (6.8 g, 21 mmol) in 40 ml of AcOH was added 5.0 g (19 mmol) of $I_2$ in 100 ml of AcOH dropwise and reaction mixture was stirred for 12 h. The reaction mixture was concentrated in vacuo, yielding a dark residue which was diluted with EtOAc and washed with aqueous $NaHCO_3$. Organic layer was dried over $MgSO_4$ and concentrated in vacuo to produce dark residue which was subjected to column chromatography ($CHCl_3$, neat) to provide 4.1 g (13 mmol, 81%) of 2,4-dinitro-6-iodoaniline.

7-Iodo-5-aminobenzimidazole. A solution of 10 g of $SnCl_2.2H_2O$ and 20 ml of HCl was added into 2,4-dinitro-6-iodoaniline (4.1 g, 13 mmol) and resulting reaction mixture was stirred at reflux for 48 h. The reaction mixture was then basified by adding 15% aq. NaOH and extracted with $CHCl_3$ several times. Combined extracts were dried over $MgSO_4$ and concentrated in vacuo, yielding. oily residue which was subjected to column chromatography (5% MeOH/EtOAc) to yield 1.1 g (4.4 mmol, 33%) of the amine. The amine was stirred at reflux in 10 ml of formic acid and 10 ml of acetic anhydride for 12 h. The reaction mixture was concentrated in vacuo to yield an oily residue which was stirred in 30 ml of HCl sat'd EtOH for 2 h. The oily reaction mixture after concentration was subjected to column chromatography (5% $NH_3$ sat'd MeOH/EtOAc) to provide 0.69 g (2.7 mmol, 60%) of the desired product.

7-Iodo-5-(2-imidazolin-2-ylamino)benzimidazole. A solution of 4-iodo-6-aminobenzimidazole (0.69 g, 2.7 mmol) and ISA (0.90 g, 6.7 mmol) was stirred at reflux for 12 h. Column chromatographic separation (30% $NH_3$ sat'd MeOH/EtOAC) of resulting reaction mixture provided 0.86 g (>99%) of the product. The product obtained was recrystallized from isopropanol to afford 0.56 g (64%) of the product as a light brown solid: mp 180–181° C.

EXAMPLE 55

7-Ethyl-5-(2-imidazolin-2-ylamino)benzimidazole (#55)

2,4-Diamino-6-ethylamine. A solution of 2,4-dinitro-6-bromoaniline (1.6 g, 6.1 mmol), tetraethyltin (2.4 ml, 12.2 mmol) and $Cl_2Pd(PPh_3)_2$ (100 mg) in 10 ml of DMF was stirred at 140° C. for 12 h. Reaction mixture was concentrated in vacuo, yielding an oil which was purified on silica gel column chromatography ($CH_2Cl_2$, neat) to provide 0.68 g (3.2 mmol, 53%) of 2,4-dinitro-6-ethylaniline, which was converted to the diamine (0.45 g, 95%) on hydrogenation ($H_2$/Pd-C).

7-Ethyl-5-aminobenzimidazole. The amine (0.46 g, 3.1 mmol) was stirred at reflux in formic acid for 12 h. The reaction mixture was concentrated n vacuo to provide an oil, which was disolved in 50 ml of HCl sat'd EtOH and stirred for 1 h. The reaction mixture was concentrated in vacuo, yielding an oil, which was subjected to column chromatography (EtOAc, neat) to provide 0.23 g (1.5 mmol, 47%) of the desired product.

7-Ethyl-5-(2-imidazolin-2-ylamino)benzimidazole. The benzimidazole (0.23 g, 1.5 mmol) and ISA (0.67 g, 5.0 mmol) was dissolved in isobutanol and stirred at reflux for 12 h. Column chromatographic separation of reaction mixture ($NH_3$ sat'd 20% MeOH/EtOAc) provided 0.30 g (1.4 mmol, 92%) of the product. The product obtained was converted to the fumarate salt and recrystallized from isopropanol to afford 0.17 g (46%) of the product as a light brown solid: mp 203–205° C.; Anal. Calc. for $C_{12}H_{15}N_5.1.0C_4H_4O_4$ requires C, 55.65; H, 5.55; N, 20.28. Found: C, 55.90; H, 5.43; N, 19.87.

EXAMPLE 56

7-Butyl-5-(2-imidazolin-2-ylamino)benzimidazole (#56)

2,4-Diamino-6-butylaniline. A solution of 2,4-dinitro-6-bromoaniline (2.0 g, 7.6 mmol), tetrabutyltin (5.3 ml, 15.2 mmol) and $Cl_2Pd(PPh_3)_2$ (100 mg) in 10 ml of DMF was stirred at 140° C. for 12 h. Reaction mixture was concentrated in vacuo, yielding an oil which was purified on silica gel column chromatography ($CH_2Cl_2$, neat) to provide 0.50 g (2.0 mmol, 27%) of 2,4-dinitro-6-butylaniline, which was converted to the diamine (0.38 g, >95%) on hydrogenation ($H_2$/Pd-C).

7-Butyl-5-aminobenzimidazole. The amine (0.46 g, 3.1 mmol) was stirred at reflux in formic acid for 12 h. reaction mixture was concentrated in vacuo to provide an oil, which was dissolved in 50 ml of HCl sat'd EtOH and stirred for 1 h. The reaction mixture was concentrated in vacuo, yielding an oil, which was subjected to column chromatography (EtOAc, neat) to provide 0.11 g (0.86 mmol, 28%) of the desired product.

7-Butyl-5-(2-imidazolin-2-ylamino)benzimidazole. The benzimidazole (0.11 g, 0.86 mmol) and ISA (0.25 g, 1.9 mmol) was dissolved in isobutanol and stirred at reflux for 12 h. Column chromatographic separation of reaction mixture ($NH_3$ sat'd 20% MeOH/EtOAc) provided 0.21 g (0.81 mmol, 95%) of the product. The product obtained was

[top of column 1:]
for $C_{11}H_{13}N_5.1.0C_4H_4O_4$ requires C, 54.38; H, 5.17; N, 21.14. Found: C, 54.02; H, 5.15; N, 20.48.

converted to the fumarate salt and recrystallized from isopropanol to afford 0.17 g (45%) of the product as a light brown solid: mp 115–117° C.; Anal. Calc. for $C_{14}H_{19}N_5 \cdot 1.5C_4H_4O_4$ requires C, 55.68; H, 5.84; N, 16.23. Found: C, 54.90; H, 5.84; N, 15.99.

EXAMPLE 57

7-Phenyl-5-(2-imidazolin-2-ylamino)benzimidazole (#57)

2,4-Diamino-6-phenylaniline. A solution of 2,4-dinitro-6-bromoaniline (2.5 g, 9.5 mmol), tetramethyltin (6.1 g, 14.3 mmol) and $Cl_2Pd(PPh_3)_2$ (100 mg) in 10 ml of DMF was stirred at 140° C. for 12 h. Reaction mixture was concentrated in vacuo, yielding an oil which was purified on silica gel column chromatography ($CH_2Cl_2$, neat) to provide 1.0 g (3.6 mmol, 41%) of 2,4-dinitro-6-phenylaniline, which was converted to the diamine (0.72 g, >95%) on hydrogenation ($H_2$/Pd-C).

7-Phenyl-5-aminobenzimidazole. The amine (0.72 g, 3.8 mmol) was stirred at reflux in formic acid for 12 h. The reaction mixture was concentrated in vacuo to provide an oil, which was dissolved in 50 ml of HCl sat'd EtOH and stirred for 1 h. The reaction mixture was concentrated in vacuo, yielding an oil, which was subjected to column chromatography (EtOAc, neat) to provide 0.48 g (2.3 mmol, 60%) of the desired product.

7-Phenyl-5-(2-imidazolin-2-ylamino)benzimidazole. The benzimidazole (0.48 g, 2.3 mmol) and ISA (1.0 g, 7.5 mmol) was dissolved in isobutanol and stirred at reflux for 12 h. Column chromatographic separation of reaction mixture ($NH_3$ sat'd 20% MeOH/EtOAc) provided 0.64 g (0.23 mmol, >95%) of the product. The product obtained was converted to the fumarate salt and recrystallized from isopropanol to afford 0.25 g (24%) of the product as a light brown solid: mp 149–151° C.; Anal. Calc. for $C_{16}H_{15}N_5 \cdot 1.5C_4H_4O_4$ requires C, 58.53; H, 4.69; N, 15.51. Found: C, 57.79; H, 4.80; N, 15.31.

EXAMPLE 58

4,7-Dibromo-5-(2-imidazolin-2-ylamino)benzimidazole (#58)

To a solution of 7-bromo-5-(2-imidazolin-2-ylamino)benzimidazole (0.6 g, 2.1 mmol) in 10 ml of ACOH was added $Br_2$ (0.057 ml, 1.1 mmol) in a portion. The resulting reaction mixture was stirred for 1 h at 25° C. Concentration of reaction mixture in vacuo yields a brown oil which was subjected to column chromatography (30% $NH_3$ sat'd MeOH/EtOAc) to provides 0.28 g (1.5 mmol, 71%) of the desired product. The product obtained was recrystallized from MeOH to afford 0.22 g (56%) of the product as a light brown solid: mp 320–321° C.; Anal. Calc. for $C_{10}H_9N_5Br_2$ requires C, 33.45; H, 2.53; N, 19.51. Found: C, 33.93; H, 4.05; N, 19.01.

EXAMPLE 59

4-Bromo-7-methyl-5-(2-imidazolin-2-ylamino)benzimidazole (#59)

4-Bromo-7-methyl-5-aminobenzimidazole. A solution of 4,7-dibromo-5-aminobenzimidazole (1.5 g, 5.1 mmol) in 10 ml of DMF was transferred into pressure bottle under $Ar_2$. To the solution was added tetramethyltin (3.6 ml, 20 mmol). and bis(triphenylphosphine)palladium(II) chloride (200 mg). The resulting reaction mixture was stirred at 140° C. for 24 h and concentrated in vacuo, yielding a dark oil which was subjected to column chromatography (40% EtOAC/$CHCl_3$) to yield 0.34 g (1.5 mmol, 29%) of the desired product as well as 0.75 g of 4,7-dimethyl-5-aminobenzimidazole.

4-Bromo-7-methyl-5-(2-imidazolin-2-ylamino)benzodiazole. A solution of the amine (0.34 g, 1.5 mmol) and ISA (0.69 g, 5.1 mmol) in 10 ml of isobutanol was stirred at reflux for 12 h. The resulting reaction mixture was purified on column chromatography (30% $NH_3$ sat'd MeOH/EtOAc) to yield 0.25 g (0.86 mmol, 57%) of the desired product. The product obtained was recrystallized from MeOH to afford 0.13 g (30%) of the product as a light brown solid: mp 242–244° C.; Anal. Calc. for $C_{11}H_{12}N_5Br$ requires C, 44.91; H, 4.11; N, 23.81. Found: C, 43.93; H, 4.05; N, 23.01.

EXAMPLE 60

4-Bromo-7-chloro-5-(2-imidazolin-2-ylamino)benzimidazole (#60).

To a solution of 7-chloro-5-(2-imidazolin-2-ylamino)benzimidazole (0.61 g, 2.6 mmol) in 10 ml of ACOH was added 0.3 ml of $Br_2$. Resulting reaction mixture was stirred for 12 h at 25° C. and concentrated in vacuo, yielding an oil, which was subjected to column chromatography ($NH_3$ sat'd 30% MeOH/EtOAc) to yield 0.23 g (0.85 mmol, 33%) of the desired product. The product obtained was converted to the fumarate salt and recrystallized from MeOH to afford 0.12 g (12%) of the product as a light yellow solid: mp 244–246° C.; Anal. Calc. for $C_{10}H_9N_5BrCl \cdot 1.0C_4H_4O_4 \cdot 0.5H_2O$ requires C, 37.77; H, 3.17; N, 18.35. Found: C, 37.75; H, 3.08; N, 18.21.

Pharmacological Profiles of the Compounds in Cloned Human Adrenergic Receptors

Binding and functional assays were performed using stably transfected human alpha adrenergic receptors. Equilibrium competition binding assays were performed with membrane preparations from cultured LM(tk–) cells stably transfected with the cloned human adrenoceptor subtypes except for $\alpha_{2b}$, which was expressed in Y-1 cells, using [$^3$H]prazosin for $\alpha_1$ receptors and [$^3$H]rauwolscine for $\alpha_2$ receptors.

EXAMPLE 61

Protocol for the Determination of the Potency of $\alpha_2$ Agonists

The activity of the compounds at the different receptors was determined in vitro using cultured cell lines that selectively express the receptor of interest. These cell lines were prepared by transfecting the cloned cDNA or cloned genomic DNA or constructs containing both genomic DNA and cDNA encoding the human alpha adrenergic receptors as described below. Table 1 shows the binding and functional activities at cloned human alpha adrenergic receptors.

$\alpha_{2A}$ Human Adrenergic Receptor: The entire coding region of $\alpha_{2A}$ (1350 bp), including 1.0 kilobasepairs of 5' untranslated sequence (5'UT) and 100 bp of 3' untranslated sequence (3'UT), was cloned into the SmaI site of the eukaryotic expression vector pCEXV-3. The insult housing this coding region was an @ 2.5 kb KpnI/HindIII human placenta genomic fragment which was end-blunted by either $T_4$ polymerase or Klenow fragment of DNA polymerase. Stable cell lines were obtained by cotransfection with the Plasmid pGCcos3neo (plasmid containing the $\alpha_{2A}$ receptor gene) and the plasmid pGCcos3neo (plasmid containing the aminoglycoside transferase gene) into LM(tk-), CHO, and NIT3T3 cells, using calcium phosphate technique. The cells were grown, in a controlled environment (37° C., 5% $CO_2$), as monolayers in Dulbecco's modified Eagle's Medium (GIBCO, Grand Island, N.Y.) containing 25 mM glucose and supplemented with 10% bovine calf serum, 100 units/ml penicillin g, and 100 µg/ml streptomycin sulfate. Stable clones were then selected for resistance to the antibiotic G-418 (1 mg/ml), and membranes were harvested and assayed for their ability to bind [$^3$H]rauwolscine as described below (see "Radioligand Binding Assays")

$\alpha_{2B}$ Human Adrenergic Receptor: The entire coding region of $\alpha_{2B}$ (1350 bp), including 393 bp of 5' untranslated sequence and 11 bp of 3' untranslated sequence, was cloned into the eukaryotic expression vector pcEXV-3 (Weinshank et al, U.S. Pat. No. 5,053,337, issued Oct. 1, 1991). Stable cell lines were selected as described above.

$\alpha_{2C}$ Human Adrenergic Receptor: The entire coding region of $\alpha_{2C}$ (1383 bp), including 2 bp of 5' UT and 400 bp of 3' UT, was cloned into the SmaI site of the eukaryotic expression vector pCEXV-3. The insert housing this coding region was an @ 1.8 kb NcoI/EcoRI human spleen genomic fragment which was end-blunted by either $T_4$ polymerase or Klenow fragment of DNA polymerase. Stable cell lines were selected as described above.

Radioligand Binding Assays: Transfected cells from culture flasks were scraped into 5 ml of 5 mM Tris-HCl, 5 mM EDTA, pH 7.5, and lysed by sonication. The cell lysates were centrifuged at 1000 rpm for 5 min at 4° C., and the supernatant was centrifuged at 30,000×g for 20 min at 4° C. The pellet was suspended in 50 mM Tris-HCl, 1 mM $MgCl_2$, and 0.1% ascorbic acid at pH 7.5. Binding of $\alpha_2$ antagonist [$^3$H]rauwolscine (0.5 mM) to membrane preparations of LM(tk-) cells was done in a final volume of 0.25 ml and incubated at 37° C. for 20 min. Nonspecific binding was determined in the presence of 10 µM phentolamine. The reaction was stopped by filtration through GF/B filters using a cell harvester. Inhibition experiments, routinely consisting of 7 concentrations of the tested compounds, were analyzed using a non-linear regression curve-fitting computer program to obtain Ki values.

Measurement of Agonist Activity: The agonist activity (expressed as $pEC_{50}$) was measured as a function of the ability to inhibit the forskolin-stimulated synthesis of cyclic adenosine monophosphate (cAMPl. The stably transfected cells were incubated in Ham's F10 with 5 mM theophylline, 10 mM HEPES, 10 µM pargyline, and/or appropriate concentrations of forskolin for 20 min at 37° C. in 5% $CO_2$. The tested compounds were then added to a final concentration of 0.001 nM to 1 µM and incubated for an additional 15 min at 37° C. in 5% $CO_2$. The medium was aspirated and the reaction was stopped by the addition of 100 mM HCl. To demonstrate competitive antagonism, a dose-response curve for norepinephrine was measured in parallel, using a fixed-dose of norepinephrine(0.32 µM). The plates are stored at 4° C. for 15 min and assayed to determine the linear concentration of cAMP. The appropriate dilution is interpolated from the standard curve of cold cAMP. The assessment of cAMP formation is determined by radioimmunoassay (cAMP radioimmunoassay kit; Advanced Magnetics, Cambridge, Mass.). Radioactivity was quantified using a Packard COBRA Auto Gamma counter, equipped with data reduction software.

$\alpha_{1A}$ Human Adrenergic Receptor: The entire coding region of $\alpha_{1A}$ (1719 bp), including 150 bp of 5' untranslated sequence (5'UT) and 300 bp of 3' untranslated sequence (3'UT), was cloned into the BamHI and ClaI sites of the polylinker-modified eukaryotic expression vector pCEXV-3, called EXJ.HR (Bard et al, International Publication No. WO 94/08040, published Apr. 14, 1994). The construct involved the ligation of partial overlapping human lymphocyte genomic and hippocampal cDNA clones: 5' sequences were contained on a 1.2 kb SmaI-XhoI genomic fragment (the vector-derived BamHI site was used for subcloning instead of the internal insert-derived SmaI site) and 3' sequences were contained on 1.3 kb XhoI-ClaI cDNA fragment (the ClaI site was from the vector polylinker). Stable cell lines were selected as described above.

$\alpha_{1B}$ Human Adrenergic Receptor: The entire coding region of $\alpha_{1B}$ (1563 bp), including 200 basepairs and 5' untranslated sequence (3' UT) and 600 bp of 3' untranslated sequence (3' UT), was cloned into the EcoRI site of pCEXV-3 eukaryotic expression vector (Bard et al, International Publication No. WO 94/08040, published Apr. 14, 1994). The construct involved ligating the full-length containing EcoRI brainstem cDNA fragment from ZapII into the expression vector. The stable cell lines were selected as described above.

$\alpha_{1C}$ Human Adrenergic Receptor: The entire coding region of $\alpha_{1C}$ (1401 bp), including 400 basepairs of 5' untranslated sequence (5' UT) and 200 p of 3' untranslated sequences (3' UT), was cloned into the KpnI site of the polylinker-modified pCEXV-3-derived eukaryotic expression vector, EXJ.RH (Bard et al, International Publication No. WO 94/08040, published Apr. 14, 1994). The construct involved ligation three partial overlapping fragments: a 5' 0.6 kb HincII genomic clone, a central 1.8 EcoRI hippocampal cDNA clone, and a 3' 0.6 Kb PstI genomic clone. The hippocampal cDNA fragment overlaps with the 5' and 3' genomic clones so that the HincII nad PstI sites at the 5' and 3' ends of the cDNA clone, respectively, were utilized for ligation. This full-length clone was cloned into the KpnI site of the expression vector, using the 5' and 3' KpnI sites of the fragment, derived from vector (i.e., pBluescript) and 3'-untranslated sequences, respectively. Stable cell lines were selected as described above.

TABLE 1

Binding and Functional Activities at Cloned Human Alpha-Adrenergic Receptors

| Ex | | Alpha-2 | | | Alpha-1 | | |
|---|---|---|---|---|---|---|---|
| | | A | B | C | A | B | C |
| 1 | pKi | 7.74 | 7.13 | 7.15 | 5.17 | 4.61 | 5.28 |
| | pEC50 | 7.24 | 7.35 | 8.56 | | | |
| | I.A | 1.00 | 1.00 | 1.00 | | | |
| 2 | pKi | 8.41 | 7.69 | 7.01 | 6.02 | 5.23 | 5.77 |
| | pEC50 | 9.53 | 7.73 | 8.93 | | | |
| | I.A | 1.00 | 1.00 | 1.00 | | | |
| 3 | pKi | 8.12 | 7.81 | 7.00 | 6.27 | 5.09 | 5.72 |
| | pEC50 | 9.18 | 7.90 | 9.25 | | | |
| | I.A | 1.00 | 1.00 | 1.00 | | | |
| 4 | pKi | 8.51 | 8.04 | 7.59 | 6.22 | 5.56 | 6.14 |
| | pEC50 | 9.41 | 8.01 | 9.45 | | | |
| | I.A | 1.00 | 1.00 | 1.00 | | | |
| 5 | pKi | 8.45 | 7.51 | 7.62 | 6.27 | 5.74 | 5.65 |
| | pEC50 | 9.05 | 7.33 | 8.87 | | | |
| | I.A | 1.00 | 1.00 | 1.00 | | | |
| 6 | pKi | 8.33 | 7.65 | 7.32 | ND | ND | ND |
| | pEC50 | 8.17 | 7.65 | 8.40 | | | |
| | I.A | 1.00 | 1.00 | 1.00 | | | |

TABLE 1-continued

Binding and Functional Activities at
Cloned Human Alpha-Adrenergic Receptors

|  |  | Alpha-2 | | | Alpha-1 | | |
| --- | --- | --- | --- | --- | --- | --- | --- |
| Ex |  | A | B | C | A | B | C |
| 7 | pKi | 8.45 | 7.55 | 7.38 | 6.57 | 5.91 | 5.75 |
|  | pEC50 | 8.14 | 6.70 | 8.21 |  |  |  |
|  | I.A | 1.00 | 1.00 | 1.00 |  |  |  |
| 8 | pKi | 7.59 | 7.30 | 6.92 | 6.17 | 5.58 | 5.75 |
|  | pEC50 | 6.87 | 6.63 | 7.68 |  |  |  |
|  | I.A | 0.90 | 0.80 | 1.00 |  |  |  |
| 9 | pKi | 7.74 | 7.33 | 6.81 | 5.56 | 4.87 | 5.17 |
|  | pEC50 | 6.65 | 7.23 | 7.92 |  |  |  |
|  | I.A | 1.00 | 1.00 | 1.00 |  |  |  |
| 10 | pKi | 8.23 | 7.55 | 7.81 | 6.21 | 5.42 | 6.07 |
|  | pEC50 | 8.52 | 6.99 | 8.63 |  |  |  |
|  | I.A | 1.00 | 1.00 | 1.00 |  |  |  |
| 11 | pKi | 7.09 | 6.65 | 5.95 | 5.00 | 4.45 | 5.24 |
|  | pEC50 | NA | NA | NA |  |  |  |
|  | I.A |  |  |  |  |  |  |
| 12 | pKi | 8.20 | 7.84 | 7.59 | 7.02 | 6.46 | 6.46 |
|  | pEC50 | 7.27 | 7.51 | 7.76 |  |  |  |
|  | I.A | 1.00 | 1.00 | 1.00 |  |  |  |
| 13 | pKi | 7.85 | 6.44 | 6.40 | 4.98 | 4.03 | 5.53 |
|  | pEC50 | NA | NA | NA |  |  |  |
|  | I.A |  |  |  |  |  |  |
| 14 | pKi | 8.02 | 6.66 | 6.64 | 5.63 | 4.69 | 6.21 |
|  | pEC50 | 6.60 | NA | NA |  |  |  |
|  | I.A | 1.00 |  |  |  |  |  |
| 15 | pKi | 6.94 | 6.14 | 6.06 | 5.19 | 4.46 | 5.31 |
|  | pEC50 | NA | NA | NA |  |  |  |
|  | I.A |  |  |  |  |  |  |
| 16 | pKi | 8.25 | 7.91 | 7.38 | 7.26 | 6.29 | 6.38 |
|  | pEC50 | 6.40 | NA | NA |  |  |  |
|  | I.A | 1.00 |  |  |  |  |  |
| 17 | pKi | 7.39 | 6.18 | 6.08 | 4.98 | 4.35 | 5.04 |
|  | pEC50 | NA | NA | NA |  |  |  |
|  | I.A | 1.00 |  |  |  |  |  |
| 18 | pKi | 8.35 | 6.43 | 6.55 | 5.57 | 4.70 | 6.05 |
|  | pEC50 | 7.08 | NA | NA |  |  |  |
|  | I.A | 0.80 |  |  |  |  |  |
| 19 | pKi | 8.33 | 6.67 | 6.89 | ND | ND | ND |
|  | pEC50 | 6.31 | NA | NA |  |  |  |
|  | I.A | 0.70 |  |  |  |  |  |
| 20 | pKi | 6.62 | 6.14 | 6.20 | 4.83 | 4.23 | 4.95 |
|  | pEC50 | NA | NA | NA |  |  |  |
|  | I.A |  |  |  |  |  |  |
| 21 | pKi | 8.19 | 7.67 | 7.26 | 6.13 | 5.33 | 5.92 |
|  | pEC50 | 6.60 | NA | NA |  |  |  |
|  | I.A | 0.90 |  |  |  |  |  |
| 22 | pKi | 8.10 | 6.37 | 6.74 | 4.98 | 3.98 | 5.73 |
|  | pEC50 | NA | NA | NA |  |  |  |
|  | I.A |  |  |  |  |  |  |
| 23 | pKi | 7.90 | 6.51 | 6.64 | 5.30 | 4.42 | 6.42 |
|  | pEC50 | 6.16 | NA | NA |  |  |  |
|  | I.A | 0.90 |  |  |  |  |  |
| 24 | pKi | 8.48 | 7.89 | 7.47 | 6.51 | 5.31 | 6.60 |
|  | pEC50 | 7.34 | NA | NA |  |  |  |
|  | I.A | 1.00 |  |  |  |  |  |
| 25 | pKi | 7.79 | 6.19 | 6.36 | 5.21 | 4.35 | 5.01 |
|  | pEC50 | NA | NA | NA |  |  |  |
|  | I.A |  |  |  |  |  |  |
| 26 | pKi | 7.93 | 6.25 | 6.59 | 5.05 | 4.24 | 5.02 |
|  | pEC50 | NA | NA | NA |  |  |  |
|  | I.A |  |  |  |  |  |  |
| 27 | pKi | 7.03 | 5.99 | 6.14 | 5.08 | 4.47 | 5.16 |
|  | pEC50 | NA | NA | NA |  |  |  |
|  | I.A |  |  |  |  |  |  |
| 28 | pKi | 8.41 | 7.38 | 7.02 | 6.18 | 4.98 | 5.42 |
|  | pEC50 | NA | NA | NA |  |  |  |
|  | I.A |  |  |  |  |  |  |
| 29 | pKi | 7.58 | 6.44 | 6.31 | 6.04 | 4.68 | 5.85 |
|  | pEC50 | NA | NA | NA |  |  |  |
|  | I.A |  |  |  |  |  |  |
| 30 | pKi | 7.76 | 6.78 | 6.51 | ND | ND | ND |
|  | pEC50 | NA | NA | NA |  |  |  |
|  | I.A |  |  |  |  |  |  |
| 31 | pKi | 8.18 | 7.43 | 7.41 | 6.59 | 5.67 | 6.43 |
|  | pEC50 | NA | NA | NA |  |  |  |
|  | I.A |  |  |  |  |  |  |
| 32 | pKi | 7.96 | 7.30 | 6.79 | 5.43 | 4.48 | 5.41 |
|  | pEC50 | NA | NA | NA |  |  |  |
|  | I.A |  |  |  |  |  |  |
| 33 | pKi | 8.47 | 7.86 | 6.79 | 5.74 | 4.48 | 5.84 |
|  | pEC50 | NA | NA | NA |  |  |  |
|  | I.A |  |  |  |  |  |  |
| 34 | pKi | 7.42 | 7.05 | 6.73 | 5.59 | 4.92 | 5.87 |
|  | pEC50 | NA | NA | NA |  |  |  |
|  | I.A |  |  |  |  |  |  |
| 35 | pKi | 8.46 | 7.80 | 7.77 | 6.51 | 5.71 | 6.10 |
|  | pEC50 | NA | NA | NA |  |  |  |
|  | I.A |  |  |  |  |  |  |
| 36 | pKi | 8.02 | 6.97 | 6.78 | 6.09 | 4.96 | 5.19 |
|  | pEC50 | 8.26 | 6.55 | NA |  |  |  |
|  | I.A | 0.60 | 0.60 |  |  |  |  |
| 37 | pKi | 8.18 | 7.09 | 6.93 | ND | ND | ND |
|  | pEC50 | 7.69 | NA | 7.28 |  |  |  |
|  | I.A | 0.60 |  | 0.50 |  |  |  |
| 38 | pKi | 7.41 | 6.28 | 5.89 | 5.14 | 4.76 | 5.17 |
|  | pEC50 | 7.45 | 6.80 | 6.44 |  |  |  |
|  | I.A | 1.00 | 0.80 | 1.00 |  |  |  |
| 39 | pKi | 7.36 | 6.31 | 6.21 | 5.80 | 4.96 | 5.32 |
|  | pEC50 | 7.61 | NA | NA |  |  |  |
|  | I.A | 0.90 |  |  |  |  |  |
| 40 | pKi | 6.40 | 6.02 | 5.55 | 5.03 | 4.57 | 5.04 |
|  | pEC50 | 6.14 | NA | NA |  |  |  |
|  | I.A | 0.80 |  |  |  |  |  |
| 42 | pKi | 7.99 | 7.63 | 6.67 | 5.79 | 5.07 | 5.09 |
|  | pEC50 | 7.63 | 7.01 | NA |  |  |  |
|  | I.A | 1.00 |  |  |  |  |  |
| 43 | pKi | 8.14 | 7.47 | 6.74 | 5.76 | 5.16 | 5.67 |
|  | pEC50 | 7.64 | 6.79 | 7.09 |  |  |  |
|  | I.A | 1.00 | 0.80 | 0.90 |  |  |  |
| 44 | pKi | 8.53 | 7.33 | 6.67 | 5.69 | 5.23 | 5.51 |
|  | pEC50 | 8.40 | 7.04 | 6.74 |  |  |  |
|  | I.A | 1.00 | 0.80 | 0.80 |  |  |  |
| 45 | pKi | 8.07 | 7.08 | 6.53 | 5.34 | 4.94 | 5.66 |
|  | pEC50 | 7.28 | 6.07 | 7.92 |  |  |  |
|  | I.A | 1.00 | 0.70 | 0.60 |  |  |  |
| 46 | pKi | 7.34 | 6.98 | 5.83 | 5.15 | 4.55 | 4.97 |
|  | pEC50 | 7.41 | 6.23 | 7.19 |  |  |  |
|  | I.A | 1.00 | 0.80 | 0.90 |  |  |  |
| 47 | pKi | 8.17 | 7.35 | 6.65 | ND | ND | ND |
|  | pEC50 | 7.33 | 6.94 | 7.34 |  |  |  |
|  | I.A | 1.00 | 0.80 | 0.80 |  |  |  |
| 48 | pKi | 7.11 | 6.18 | 6.61 | 5.91 | 7.31 | 6.92 |
|  | pEC50 | NA | 6.70 | 8.87 |  |  |  |
|  | I.A |  | 0.80 | 0.60 |  |  |  |
| 49 | pKi | 7.71 | 7.44 | 6.67 | ND | ND | ND |
|  | pEC50 | 7.04 | NA | 7.65 |  |  |  |
|  | I.A | 0.80 |  | 1.00 |  |  |  |
| 50 | pKi | 8.16 | 8.63 | 7.61 | 7.45 | 6.78 | 6.11 |
|  | pEC50 | 7.80 | 7.68 | 7.15 |  |  |  |
|  | I.A | 1.00 | 0.90 | 1.00 |  |  |  |
| 51 | pKi | 7.58 | 7.56 | 6.91 | ND | ND | ND |
|  | pEC50 | 7.01 | 7.05 | 8.37 |  |  |  |
|  | I.A | 0.90 | 0.60 | 1.00 |  |  |  |
| 52 | pKi | 7.61 | 7.11 | 6.90 | ND | ND | ND |
|  | pEC50 | 7.09 | 7.14 | 8.26 |  |  |  |
|  | I.A | 0.90 | 0.80 | 1.00 |  |  |  |
| 53 | pKi | 7.83 | 7.74 | 7.05 | 6.51 | 5.72 | 6.00 |
|  | pEC50 | 7.24 | 7.74 | 8.97 |  |  |  |
|  | I.A | 1.00 | 1.00 | 1.00 |  |  |  |
| 54 | pKi | 7.31 | 7.56 | 6.70 | ND | ND | ND |
|  | pEC50 | 5.90 | 6.88 | 7.69 |  |  |  |
|  | I.A | 0.70 | 0.60 | 0.90 |  |  |  |
| 55 | pKi | 7.36 | 6.68 | 6.37 | ND | ND | ND |
|  | pEC50 | 7.29 | NA | 6.79 |  |  |  |
|  | I.A | 0.60 |  | 0.80 |  |  |  |

TABLE 1-continued

Binding and Functional Activities at
Cloned Human Alpha-Adrenergic Receptors

| Ex | | Alpha-2 | | | Alpha-1 | | |
|----|--------|------|------|------|------|------|------|
|    |        | A    | B    | C    | A    | B    | C    |
| 56 | pKi    | 7.66 | 6.74 | 6.69 | 5.90 | 5.29 | 6.23 |
|    | pEC50  | 6.30 | 6.86 | 7.89 |      |      |      |
|    | I.A    | 0.70 | 0.30 | 1.00 |      |      |      |
| 57 | pKi    | 7.78 | 7.22 | 6.87 | ND   | ND   | ND   |
|    | pEC50  | NA   | 5.07 | 7.82 |      |      |      |
|    | I.A    |      | 0.50 | 1.00 |      |      |      |
| 58 | pKi    | 8.89 | 8.76 | 7.51 | ND   | ND   | ND   |
|    | pEC50  | 8.61 | 7.55 | 8.49 |      |      |      |
|    | I.A    | 1.00 | 0.50 | 1.00 |      |      |      |
| 59 | pKi    | 9.01 | 8.10 | 7.78 | ND   | ND   | ND   |
|    | pEC50  | 9.08 | 7.39 | 8.89 |      |      |      |
|    | I.A    | 1.00 | 0.90 | 1.00 |      |      |      |
| 60 | pKi    | 9.05 | 9.33 | 7.79 | 6.85 | 6.5  | 6.32 |
|    | pEC50  | 9.23 | 7.75 | 9.4  |      |      |      |
|    | I.A    | 1    | 0.9  | 1    |      |      |      |
| C  | pKi    | 8.03 | 8.09 | 7.52 | 6.29 | 5.62 | 6.01 |
|    | pEC50  | 8.09 | 6.79 | 7.26 |      |      |      |
|    | I.A    | 1    | 1    | 1    |      |      |      |

NA: Not Active
ND: Not Determined
C: Clonidine

The protocols used to obtain these data are described in Example 61.

EXAMPLE 62

Assay to Measure Analgesic Activity of Test Compounds

Warm-Water Tail Withdrawal Assay (Butelman, E. R.; Woods, J. H. *J. Pharmacol. Exp. Therapeut.* 1993, 264, 7620)

Subjects. Adult rhesus monkeys (Macaca. mulatta) of either sex were housed individually with free access to water. They were fed fresh fruit weekly and approximately 40 biscuits (Purina Monkey Chow) daily.

Apparatus and procedure. Tail withdrawal latencies were timed manually using a microprocessor (IBM PCjr) via a push button switch. Monkeys were seated in primate restraining chairs, and the lower portion of the shaved tail (approximately 10 cm) was immersed in a thermos flask containing water maintained at either 40, 50 or 55° C. A maximum allowed latency of 20 seconds was recorded if the monkeys failed to remove their tails by this time. Sessions began with control determinations at each water temperature, presented in a varied order between the subjects. In order for a subject to be used, its withdrawal latency at 40° C. had to reach 20 seconds. After control determinations, drugs were administered every 30 minutes using a cumulative dosing procedure in which doses increased in 0.25 or 0.5 log units with each cycle. Fifteen minutes after each injection, the subjects were tested at the three temperatures in varying order, with tests being separated from each other by approximately 2 minutes. In time course studies, a single drug dose was administered after control determination, with testing following at 30 minute intervals.

Design. Clonidine and compound 4 were studied up to doses that produced near maximal withdrawal latencies in 55° C. water. The same three subjects were studied in all the above experiments.

Sedation and Muscle Relaxation

Procedure. Monkeys were trained to receive subcutaneous injections while in their home cages; they were rated by one non-blind observer familiar with the individual subjects, according to modified rating scales for sedation and muscle relaxation (Table 2). Separate scales describe increasing degrees of sedation (as measured by responsiveness to stimuli) and muscle relaxation (as observed through changes in posture). Animals were injected in a cumulative dosing procedure with a 30 minute interinjection interval; observer rating on both scales took place approximately 15 minutes after each injection.

Design. Clonidine (0.032–1.0 mg/kg) and compound 4 (0.1–3.2 mg/kg) were studied using a cumulative dosing procedure. The same three monkeys were typically studied under each se of conditions.

Results: Using the procedures described above, compound 4 was found to be an effective analgesic agent with decreased sedation relative to the reference compound, clonidine.

TABLE 2

Modified sedation and muscle relaxation rating scales

| Grade | Sedation |
|-------|----------|
| 0 | No observable sedation |
| 1 | Monkey appears to stare into space |
| 2 | Monkey is inattentive to ordinary movements of observer |
| 3 | Monkey responds only to loud noises in the room |
| 4 | Monkey responds only to opening of cage latch |
| 5 | Monkey responds only to loud noises near its ear |
| 6 | Monkey responds only to touch |

| Grade | Muscle Relaxation |
|-------|-------------------|
| 0 | No observable muscle relaxation |
| 1 | Slight facial relaxation, jaw slackening, shoulder droop |
| 2 | Pronounced facial relaxation, jaw slackening, shoulder droop |
| 3 | Monkey must brace itself to sit up |
| 4 | Monkey cannot sit up |

What is claimed is:

1. A compound having the structure:

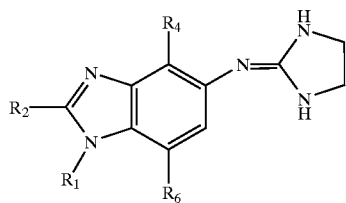

wherein each of $R_1$ and $R_2$ is independently H; straight chain or branched, substituted or unsubstituted $C_1$–$C_7$ alkyl, $C_2$–$C_7$ alkenyl or alkynyl;

wherein $R_4$ is H, F, Cl, Br, I; straight chain or branched, substituted or unsubstituted $C_2$–$C_7$ alkynyl;

wherein $R_6$ is H, F, Cl, Br, I; straight chain or branched, substituted or unsubstituted $C_1$–$C_7$ alkyl, or $C_2$–$C_7$ alkenyl or alkynyl; and wherein if any substituent is present it is selected from the group consisting of F, –$NH_2$, –OH, cyclohexyl, phenyl or methoxyphenyl.

2. The compound of claim 1, wherein $R_6$ is H.

3. The compound of claim 2, wherein $R_1$ is H or straight chain or branched, substituted or unsubstituted $C_1$–$C_7$ alkyl;

$R_2$ is H, methyl, ethyl, isopropyl, tert-butyl, trifluoromethyl, cyclopropyl or diphenylmethyl; and $R_4$ is H, F, Cl, Br, or I.

4. The compound of claim 3, wherein $R_2$ is H.

5. The compound of claim 4, wherein $R_4$ is Br.

6. The compound of claim 5, wherein $R_1$ is straight chain or branched, substituted or unsubstituted $C_1$–$C_7$ alkyl.

7. The compound of claim 6, wherein $R_1$ is $CH_3$.

8. The compound of claim 1, having the structure:

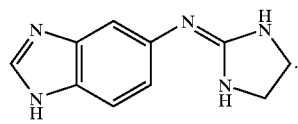

9. A pharmaceutical composition comprising a therapeutically effective amount of the compound of any one of claims 1-8 and a pharmaceutically acceptable carrier.

10. A method for treating an alpha-2 adrenergic receptor associated disorder in a subject which comprises administering to the subject a therapeutically effective amount of the compound of any one of claims 1-8 so as to thereby treat the alpha-2 adrenergic receptor associated disorder.

11. The methof of claim 10, wherein the alpha-2 adrenergic receptor associated disorder is migraine, hypertension, alcohol withdrawl, drug addiction, rheumatoid arthritis, ischemia, spasticity, diarrhea or nasal congenstion.

12. A method of treating nasal congenstion in a subject which comprises administering to the subject am amount of the compoud of any one of claims 1–8 effective to treat the sunject's nasal congestion.

13. A method for alleviating pain in a subject which comprises administering to the subject an amount of a compound of any one of claims 1–8 effective to alleviate the subject's pain.

* * * * *

UNITED STATES PATENT AND TRADEMARK OFFICE
CERTIFICATE OF CORRECTION

PATENT NO.    : 6,495,583 B1  
DATED         : December 17, 2002  
INVENTOR(S)   : Yoon T. Jeon and Charles Gluchowski Page 1 of 1

It is certified that error appears in the above-identified patent and that said Letters Patent is hereby corrected as shown below:

Column 41,
Lines 12-18, the structure shown as

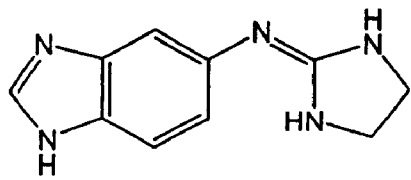 should read 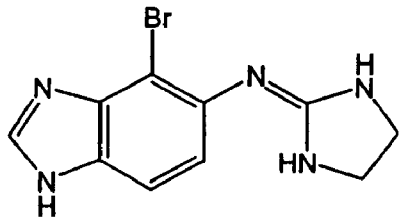

Column 42,
Line 7, "methof of" should read -- method of --

Signed and Sealed this

Thirteenth Day of May, 2003

JAMES E. ROGAN  
*Director of the United States Patent and Trademark Office*